(12) United States Patent
Belldegrun et al.

(10) Patent No.: US 10,035,981 B2
(45) Date of Patent: *Jul. 31, 2018

(54) KIDNEY-SPECIFIC TUMOR VACCINE DIRECTED AGAINST KIDNEY TUMOR ANTIGEN G-250

(71) Applicant: The Regents of the University of California, Oakland, CA (US)

(72) Inventors: Arie Belldegrun, Los Angeles, CA (US); Cho-Lea Tso, Torrance, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/200,885

(22) Filed: Jul. 1, 2016

(65) Prior Publication Data

US 2016/0376556 A1 Dec. 29, 2016

Related U.S. Application Data

(60) Division of application No. 14/268,662, filed on May 2, 2014, now Pat. No. 9,409,965, which is a continuation of application No. 12/479,415, filed on Jun. 5, 2009, now Pat. No. 8,741,306, which is a division of application No. 09/783,708, filed on Feb. 13, 2001, now Pat. No. 7,572,891.

(60) Provisional application No. 60/182,636, filed on Feb. 15, 2000, provisional application No. 60/182,429, filed on Feb. 14, 2000.

(51) Int. Cl.
| | |
|---|---|
| *C12N 5/0783* | (2010.01) |
| *A61K 39/00* | (2006.01) |
| *C07K 14/47* | (2006.01) |
| *C07K 14/535* | (2006.01) |
| *A61K 9/00* | (2006.01) |
| *C12N 15/85* | (2006.01) |
| *A61K 38/00* | (2006.01) |

(52) U.S. Cl.
CPC .......... *C12N 5/0636* (2013.01); *A61K 9/0019* (2013.01); *A61K 39/0011* (2013.01); *C07K 14/47* (2013.01); *C07K 14/4748* (2013.01); *C07K 14/535* (2013.01); *C12N 15/85* (2013.01); *A61K 38/00* (2013.01); *A61K 2039/5154* (2013.01); *A61K 2039/5158* (2013.01); *A61K 2039/53* (2013.01); *A61K 2039/54* (2013.01); *A61K 2039/55516* (2013.01); *A61K 2039/55522* (2013.01); *A61K 2039/6031* (2013.01); *C12N 2501/22* (2013.01)

(58) Field of Classification Search
None
See application file for complete search history.

(56) References Cited

U.S. PATENT DOCUMENTS

| | | | |
|---|---|---|---|
| 5,616,477 | A | 4/1997 | Price |
| 5,972,353 | A | 10/1999 | Zavada et al. |
| 7,250,291 | B1 | 7/2007 | Dranoff et al. |
| 7,572,891 | B2 | 8/2009 | Belldegrun et al. |
| 8,741,306 | B2 | 6/2014 | Belldegrun et al. |
| 8,711,306 | B2 | 7/2014 | Oohira et al. |
| 2015/0010587 | A1 | 1/2015 | Belldegrun et al. |

FOREIGN PATENT DOCUMENTS

| | | | |
|---|---|---|---|
| WO | 95/34650 | A2 | 12/1995 |
| WO | 95/34650 | A3 | 12/1995 |
| WO | 2005/037083 | A2 | 4/2005 |
| WO | 2005/037083 | A3 | 4/2005 |

OTHER PUBLICATIONS

Amato, Robert J. Vaccine Therapy for Renal Cell Carcinoma. Reviews in Urology 5(2): 65-71, 2003.*
Tso et al. Induction of G250-targeted and T-Cell-mediated Antitumor Activity against Renal Cell Carcinoma Using a Chimeric Fusion Protein Consisting of G250 and Granulocyte/Monocyte-Colony Stimulating Factor. Cancer Research 61: 7925-7933, Nov. 1, 2001.*
Batova et al. (1999) "The Ch14.18-GM-CSF Fusion Protein Is Effective at Mediating Antibody-dependent Cellular Cytotoxicity and Complement-dependent Cytotoxicity in Vitro" Clin. Cancer Res., 5:4256-4263.
Battaglia et al. (2000) "The fusion protein MEN 11303 (granulocyte-macrophage colony stimulating factor/erythropoietin) acts as a potent inducer of erthropoiesis" Exp. Hematol., 28:490-498.
Bhattacharya-Chatterjee M et al Curr Opin Mol Ther. Feb. 2001;3(1):63-9).
Bowne et al. (1999) "Injection of DNA encoding granulocyte-macrophage colony stimulating factor recruits dendritic cells for immune adjuvant effects" Cytokines Cellu. Mol Ther., 5:217-225.
Brändle et al. (1996) "A Mutated HLA-A2 Molecule Recognized by Autologous Cytotoxic T Lymphocytes on a Human Renal Cell Carcinoma" J. Exp. Med., 183:2501-2508.
Brossart et al. (1998) "Her-2/neu-derived peptides are tumor-associated antigens expressed by human renal cell and colon carcinoma lines and are recognized by in vitro induced specific cytotoxic T lymphocytes" Cancer Res., 58:732-736.
Cao et al. (1999) "Therapy of established tumour with a hybrid cellular vaccine generated by using granulocyte-macrophage colony stimulating factor genetically modified dendritic cells" Immunol., 97:616-625.
Condon et al. (1996) "DNA-based immunization by in vivo transfection of dendritic cells" Nature Med., 2(10):1122-1128.

(Continued)

*Primary Examiner* — Alana Harris Dent
(74) *Attorney, Agent, or Firm* — Kilpatrick Townsend & Stockton LLP

(57) ABSTRACT

This invention provides an anti-cancer immunogenic agent(s) (e.g. vaccines) that elicit an immune response specifically directed against renal cell cancers expressing a G250 antigenic marker. Preferred immunogenic agents comprise a chimeric molecule comprising a kidney cancer specific antigen (G250) attached to a granulocyte-macrophage colony stimulating factor (GM-CSF). The agents are useful in a wide variety of treatment modalities including, but not limited to protein vaccination, DNA vaccination, and adoptive immunotherapy.

18 Claims, 13 Drawing Sheets

(56) References Cited

OTHER PUBLICATIONS

Fisher et al. (1997) "High-Dose Aldesleukin in Renal Cell Carcinoma: Long Term Survival Update" Cancer J. Sci. Amer., 3: S70.
Gaugler et al. (1996) "A new gene coding for an antigen recognized by autologus cytolytix T lymphocytes on a human renal carcinoma" Immunogenetics, 44:323-330.
Grabmaier et al., (2000) "Molecular Cloning and Immunogenicity of Renal Cell Carcinoma-Associated Antigen G250" Int. J. Cancer, 85: 865-870.
Hall et al. (1999) "DT388-GM-CSF, a novel fusion toxin consisting of a truncated diphtheria toxin fused to human granulocyte-macrophage colony-stimulating factor, prolongs host survival in a SCID mouse model of acute myeloid leukemia." Leukemia, 13: 629-633.
Hernández, J.M. et al., "Novel Kidney Cancer Immunotherapy Based on the Granulocyte-Macrophage Colony-stimulating Factor and Carbonic Anhydrase IX Fusion Gene," Clinical Cancer Research, May 2003, vol. 9, pp. 1906-1916.
Hill et al. (1995) "The effect of granulocyte-macrophage colony-stimulating factor on myeloid cells and its clinical applications." J. Leukocyte Biol. 58: 634-642.
Hinkel et al. (2000) "Immunomodulatory Dendritic Cells Generated from Nonfractionalized Bulk Peripheral Blood Mononuclear Cell Cultures Induce Growth of Cytotoxic T Cells Against Renal Cell Carcinoma." J. Immunother., 23(1); 83-93.
Huang et al. (1994) "Role of Bone Marrow Derived Cells in Presenting MHC Class-1 Restricted Tumor Antigens." Science, 264: 961-965.
International Search Report dated Oct. 8, 2008, for International Application No. PCT/US07/88676, filed on Dec. 21, 2007, 6 pages.
Jonuleit et al. (1996) "Cytokines and their effects on maturation, differentiation and migration of dentritic cells." Archives of Dermatological Res. 289: 1-8.
Lee et al. (1999) "Increased Vaccine-Specific T Cell Frequency After Peptide-Based Vaccination Correlates with Increased Susceptibility to In Vitro Stimulation But Does Not Lead to Tumor Regression." J Immunol., 163: 6292-6300.
Liu (1998) "Vaccine developments" Nature Med., 4(5): 515-519.
Luo et al. (2000) "Synthetic DNA delivery systems." Nature Biotechnology, 18: 33-37.
Mach et al. (2000) "Differences in Dendritic Cells Stimulated in Vivo by Tumors Engineered to Secrete Granulocyte-Macrophage Colony-stimulating Factor or Flt3-Ligand" Cancer Res., 60: 3239-3246.
Mulders et al. (1999) "Presentation of Renal Tumor Antigens by Human Dendritic Cells Activates Tumor-infiltrating Lymphocytes against Autologous Tumor: Implications for Live Kidney Cancer Vaccines" Clin. Cancer Res., 5:445-454.
Nestle et al. (1998) "Vaccination of melanoma patients with peptide- or tumor lysate-pulsed dendritic cells." Nature Med., 4(3): 328-332.
Opavsk et al. (1996) "Human MN/CA9 Gene, a Novel Member of the Carbonic Anhydrase Family: Structure and Exon to Protein Domain Relationships." Genomics, 33: 480-487.
Parhar et al. (1992) "Anti-tumor cytotoxic potential and effect on human bone marrow GM-CFU of human LAK cells generated in response to various cytokines" Europ. Cytokine Network, 3(3): 299-306.
Parkhurst et al. (1996) "Improved Induction of Melanoma-Reactive CTL with Peptides from the Melanoma Antigen gp100 Modified at HLA-A*0201-Binding Residues." J. Immunol., 157: 2539-2548.
Pulendran et al. (1999) "Distinct dendritic cell subsets differentially regulate the class of immune response in vivo" Proc. Natl. Acad. Sci. USA, 96:1036-1041.
Rammensee et al. (1993) "Peptides Naturally Presented by MHC Class I Molecules." Annual Rev. Immunol., 11: 213-244.
Rescigno et al. (1998) "Dendritic Cell Survival and Maturation Are Regulated by Different Signaling Pathways." J. Exp. Med., 188(11): 2175-2180.
Rosenberg et al., (1999) "Impact of Cytokine Administration on the Generation of Antitumor Reactivity in Patients with Metastatic Melanoma Receiving a Peptide Vaccine." J. Immunol., 163:1690-1695.
Roth et al., (2000) "Granulocyte Macrophage Colony-stimulating Factor and Interleukin 4 Enhance the Number and Antigen-presenting Activity of Circulating CD14+ and CD83+ Cells in Cancer Patients" Cancer Res., 60:1934-1941.
Roussel et al. (1990) "Long-term cultures of human peripheral blood lymphocytes with recombinant human interleukin-2 generated a population of virtually pure CD3+ CD16– CD56– large granular lymphocyte LAK cells" Clin. Exp. Immunol., 82: 416-421.
Simons et al., (1997) "Bioactivity of autologous irradiated renal cell carcinoma vaccines generated by ex vivo granulocyte-macrophage colony-stimulating factor gene transfer" Cancer Res. 57: 1537-1546.
Soiffer et al. (1998) "Vaccination with irradiated autologous melanoma cells engineered to secrete human granulocyte-macrophage colony-stimulating factor generates potent antitumor immunity in patients with metastatic melanoma" Proc. Natl. Acad. Sci. USA, 95: 13141-13146.
Steger et al (Br. J. Cancer 1995; 72:101-107).
Tao et al (Nature Apr. 1993, 362:755-758).
Tripathi et al. (1999) "Construction and characterization of a chimeric fusion protein consisting of an anti-idiotype antibody mimicking a break cancer-associated antigen and the cytokine GM-CSF" Hybridoma 18(12): 193-202.
Uemura et al (Br J Cancer Oct. 1999;81(4):741-6).
Ulmer et al. (1998) "Protective CD4+ and CD8+ T Cells against Influenza Virus Induced by Vaccination with Nucleoprotein DNA" J Virol., 72(7): 5648-5653.
Vissers et al. (1999) "The Renal Cell Carcinoma-associated Antigen G250 Encodes a Human Leukocyte Antigen (HLA)-A2. 1-restricted Epitope Recognized by Cytotoxic T Lymphocytes" Cancer Res., 59:5554-5559.
Wang et al. (1999) "Human tumor antigens: implications for cancer vaccine development" J. Mol. Med., 77:640-655.
Wong et al. (1985) "Human GM-CSF: Molecular Cloning of the Complementary DNA and Purification of the Natural and Recombinant Proteins" Science 228: 810-815.
Xu et al. (2000) "Genetic modulation of tumor antigen presentation" Trends in Biotech. 18: 167-172.
Yang et al. (1999) "Murine dendritic cells transfected with human GP100 elicit both antigen-specific CB8+ and CD4+ T-cell responses and are more effective than DNA vaccines at generating anti-tumor immunity," Intl. J. Cancer, 83: 532-540.
Yang et al., (2000) "Dendritic cells infected with a vaccinia vector carrying the human gp100 gene simultaneously present multiple specificities and elicit high-affinity T cells reactive at multiple epitopes and restricted by HLA-A2 and -A3." J. Immunol., 164(8): 4204-4211.
Zhou et al., (1996) "RNA Melanoma Vaccine: Induction of Antitumor Immunity by Human Glycoprotein 100 mRNA Immunization" Human Gene Ther., 10: 2719-2724.
Zisman, Amnon et al., "Immune and Genetic Therapies for Advanced Renal Cell Carcinoma," Rev Urol. (Winter 2002); 2(1):54-59.

* cited by examiner

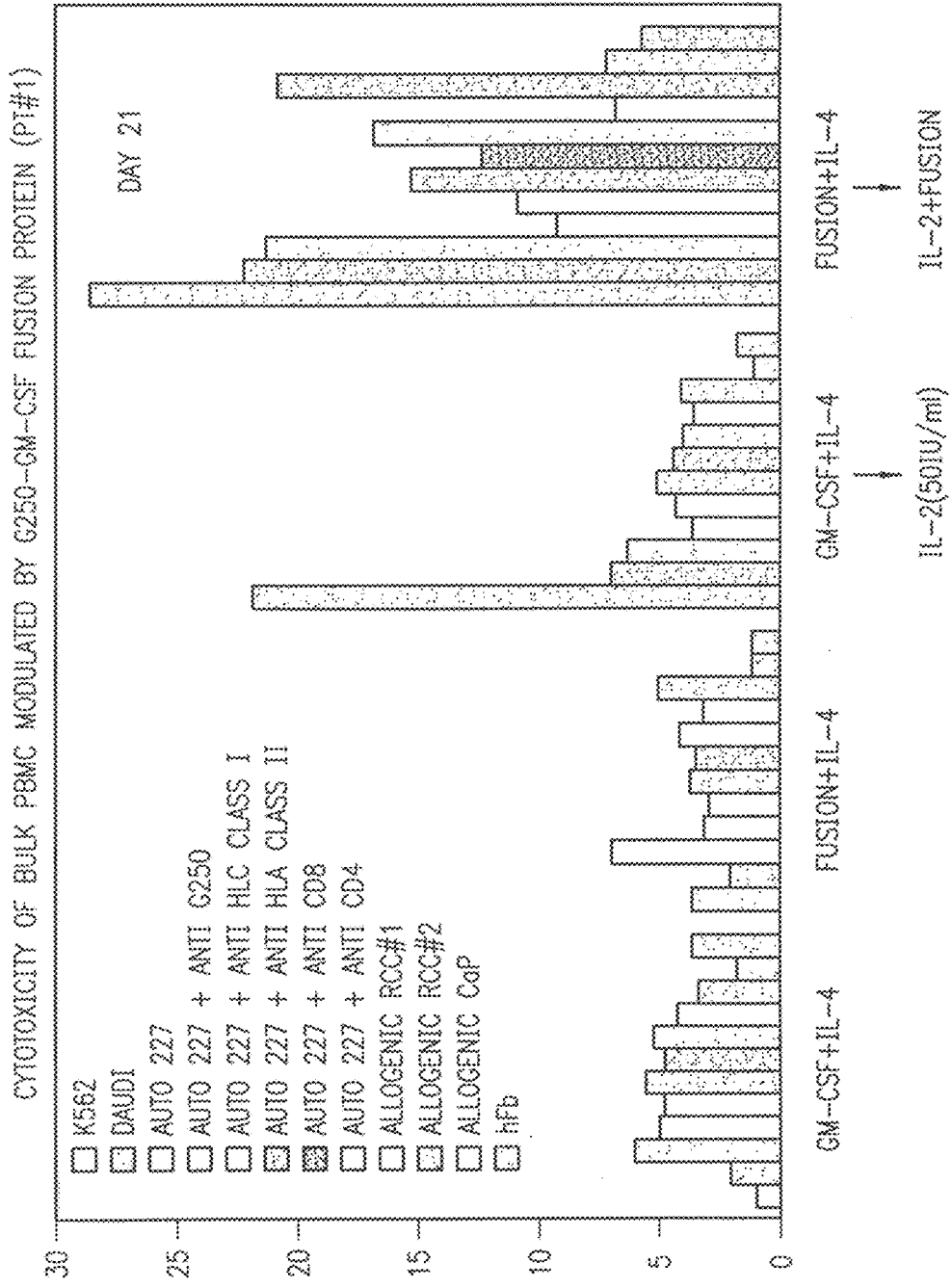

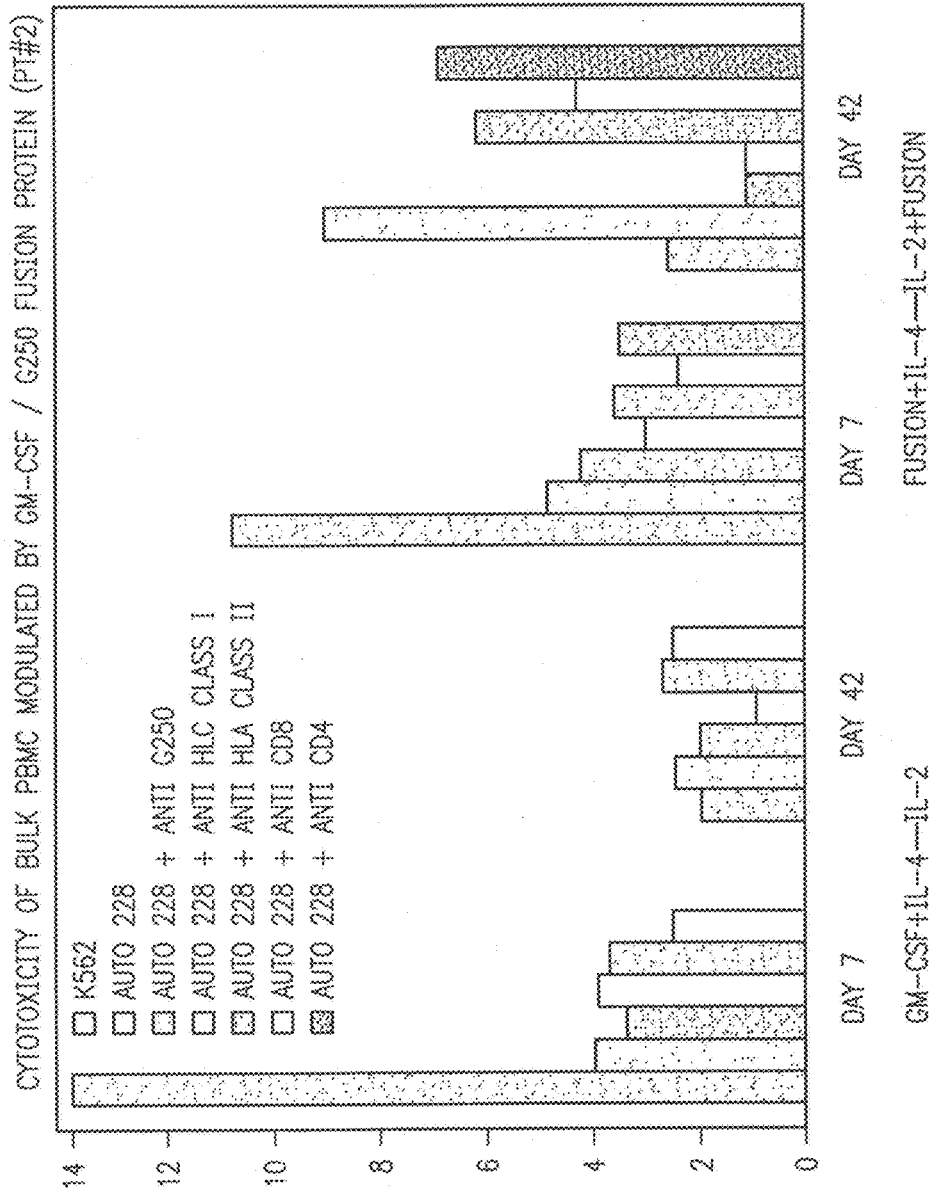

FIG. 6A
INFECTED CELLS/ANTI-G250
INFECTED CELLS/ANTI-GM-CSF
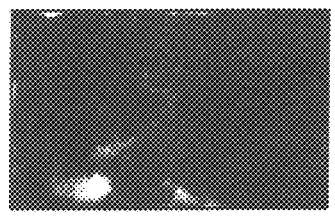
NON INFECTED CELLS
ANTI-GM-CSF/ANTI-G250
FIG. 6B
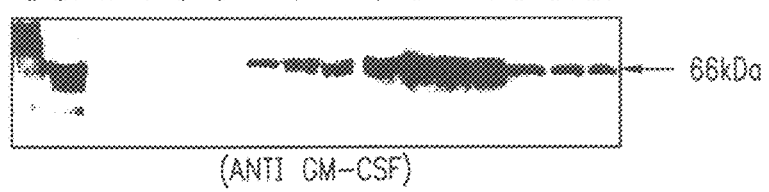
FIG. 6C
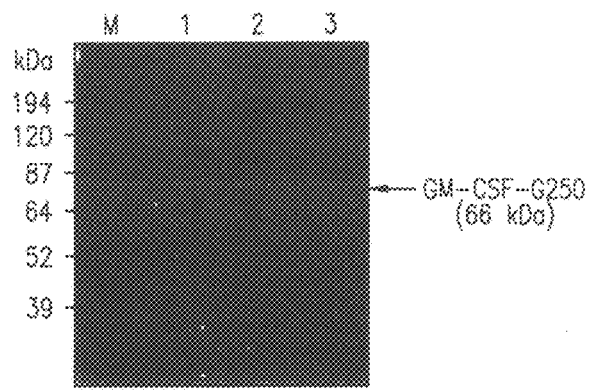

SEQUENCE LISTING

```
<160> NUMBER OF SEQ ID NOS: 27

<210> SEQ ID NO 1
<211> LENGTH: 604
<212> TYPE: PRT
<213> ORGANISM: Artificial Sequence
<220> FEATURE:
<223> OTHER INFORMATION: Description of Artificial Sequence:G250-GM-CSF
      fusion protein, fusion protein expressed by GM-CSF gene fragment
      (Accession #E02287) linked to G250 gene sequence (Accession
      #X66839) through 6 nucleotides coding for Ala

<400> SEQUENCE: 1

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
```

-continued

```
                20                  25                  30
Val Asn Ala Ile Gln Glu Ala Arg Arg Leu Leu Asn Leu Ser Arg Asp
         35                  40                  45
Thr Ala Ala Glu Met Asn Glu Thr Val Glu Val Ile Ser Glu Met Phe
 50                  55                  60
Asp Leu Gln Glu Pro Thr Cys Leu Gln Thr Arg Leu Glu Leu Tyr Lys
 65                  70                  75                  80
Gln Gly Leu Arg Gly Ser Leu Thr Lys Leu Lys Gly Pro Leu Thr Met
                 85                  90                  95
Met Ala Ser His Tyr Lys Gln His Cys Pro Pro Thr Pro Glu Thr Ser
                100                 105                 110
Cys Ala Thr Gln Ile Ile Thr Phe Glu Ser Phe Lys Glu Asn Leu Lys
             115                 120                 125
Asp Phe Leu Leu Val Ile Pro Phe Asp Cys Trp Glu Pro Val Gln Glu
             130                 135                 140
Ala Ala Ala Pro Leu Cys Pro Ser Pro Trp Leu Pro Leu Leu Ile Pro
145                 150                 155                 160
Ala Pro Ala Pro Gly Leu Thr Val Gln Leu Leu Leu Ser Leu Leu Leu
                165                 170                 175
Leu Met Pro Val His Pro Gln Arg Leu Pro Arg Met Gln Glu Asp Ser
             180                 185                 190
Pro Leu Gly Gly Gly Ser Ser Gly Glu Asp Pro Leu Gly Glu Glu
             195                 200                 205
Asp Leu Pro Ser Glu Glu Asp Ser Pro Arg Glu Glu Asp Pro Pro Gly
 210                 215                 220
Glu Glu Asp Leu Pro Gly Glu Glu Asp Leu Pro Gly Glu Glu Asp Leu
225                 230                 235                 240
Pro Glu Val Lys Pro Lys Ser Glu Glu Gly Ser Leu Lys Leu Glu
                245                 250                 255
Asp Leu Pro Thr Val Glu Ala Pro Gly Asp Pro Gln Glu Pro Gln Asn
                260                 265                 270
Asn Ala His Arg Asp Lys Glu Gly Asp Asp Gln Ser His Trp Arg Tyr
             275                 280                 285
Gly Gly Asp Pro Pro Trp Pro Arg Val Ser Pro Ala Cys Ala Gly Arg
             290                 295                 300
Phe Gln Ser Pro Val Asp Ile Arg Pro Gln Leu Ala Ala Phe Cys Pro
305                 310                 315                 320
Ala Leu Arg Pro Leu Glu Leu Leu Gly Phe Gln Leu Pro Pro Leu Pro
                325                 330                 335
Glu Leu Arg Leu Arg Asn Asn Gly His Ser Val Gln Leu Thr Leu Pro
             340                 345                 350
Pro Gly Leu Glu Met Ala Leu Gly Pro Gly Arg Glu Tyr Arg Ala Leu
             355                 360                 365
Gln Leu His Leu His Trp Gly Ala Ala Gly Arg Pro Gly Ser Glu His
             370                 375                 380
Thr Val Glu Gly His Arg Phe Pro Ala Glu Ile His Val Val His Leu
385                 390                 395                 400
Ser Thr Ala Phe Ala Arg Val Asp Glu Ala Leu Gly Arg Pro Gly Gly
                405                 410                 415
Leu Ala Val Leu Ala Ala Phe Leu Glu Glu Gly Pro Glu Glu Asn Ser
             420                 425                 430
Ala Tyr Glu Gln Leu Leu Ser Arg Leu Glu Glu Ile Ala Glu Glu Gly
             435                 440                 445
```

```
Ser Glu Thr Gln Val Pro Gly Leu Asp Ile Ser Ala Leu Leu Pro Ser
    450                 455                 460

Asp Phe Ser Arg Tyr Phe Gln Tyr Glu Gly Ser Leu Thr Thr Pro Pro
465                 470                 475                 480

Cys Ala Gln Gly Val Ile Trp Thr Val Phe Asn Gln Thr Val Met Leu
                485                 490                 495

Ser Ala Lys Gln Leu His Thr Leu Ser Asp Thr Leu Trp Gly Pro Gly
                500                 505                 510

Asp Ser Arg Leu Gln Leu Asn Phe Arg Ala Thr Gln Pro Leu Asn Gly
            515                 520                 525

Arg Val Ile Glu Ala Ser Phe Pro Ala Gly Val Asp Ser Ser Pro Arg
        530                 535                 540

Ala Ala Glu Pro Val Gln Leu Asn Ser Cys Leu Ala Ala Gly Asp Ile
545                 550                 555                 560

Leu Ala Leu Val Phe Gly Leu Leu Phe Ala Val Thr Ser Val Ala Phe
                565                 570                 575

Leu Val Gln Met Arg Arg Gln His Arg Arg Gly Thr Lys Gly Gly Val
                580                 585                 590

Ser Tyr Arg Pro Ala Glu Val Ala Glu Thr Gly Ala
            595                 600
```

<210> SEQ ID NO 2
<211> LENGTH: 1833
<212> TYPE: DNA
<213> ORGANISM: Artificial Sequence
<220> FEATURE:
<223> OTHER INFORMATION: Description of Artificial Sequence:G250-GM-CSF
      fusion protein, expression cassette of GM-CSF gene fragment
      (Accession #E02287) joined to G250 gene (Accession #X66839) by 6
      nucleotide linker

<400> SEQUENCE: 2

```
atgtggctgc agagcctgct gctcttgggc actgtggcct gcagcatctc tgcacccgcc      60
cgctcgccca gccccagcac gcagccctgg gagcatgtga atgccatcca ggaggcccgg     120
cgtctcctga acctgagtag agacactgct gctgagatga tgaaacagt agaagtcatc      180 tcagaaatgt ttgacctcca ggagccgacc tgcctacaga cccgcctgga gctgtacaag     240
cagggcctgc ggggcagcct caccaagctc aagggcccct tgaccatgat ggccagccac     300
tacaagcagc actgccctcc aaccccggaa acttcctgtg caacccagat atcacctttt     360
gaaagtttca agagaaacct gaaggacttt ctgcttgtca tcccctttga ctgctgggag     420
ccagtccagg aggcggccgc tcccctgtgc cccagccct ggctccctct gttgatcccg      480
gcccctgctc caggcctcac tgtgcaactg ctgctgtcac tgctgcttct gatgcctgtc     540
catccccaga ggttgccccg gatgcaggag gattcccct gggaggagg ctcttctggg       600 gaagatgacc cactgggcga ggaggatctg cccagtgaag aggattcacc agagaggag      660 gatccacccg agaggagga tctacctgga ggaggaatc tacctggaga ggaggatcta      720
cctgaagtta agcctaaatc agaagaagag ggctccctga gttaggga tctacctact      780 gttgaggctc ctggagatcc tcaagaaccc cagaataatg cccacaggga caaaaaggg     840 gatgaccaga gtcattggcg ctatggaggc gacccgccct ggccccgggt gtccccagcc     900
tgcgcgggcc gcttccagtc cccggtggat atccgccccc agctcgccgc cttctgcccg     960
gccctgcgcc cctgaact cctgggcttc cagctcccgc cgtcccaga actgcgcctg       1020 cgcaacaatg ccacagtgt gcaactgacc ctgcctcctg gctagagat ggctctgggt      1080
```

```
cccgggcggg agtaccgggc tctgcagctg catctgcact gggggggctgc aggtcgtccg    1140 ggctcggagc acactgtgga aggccaccgt ttccctgccg agatccacgt ggttcacctc    1200
agcaccgcct ttgccagagt tgacgaggcc ttggggcgcc cgggaggcct ggccgtgttg    1260
gccgcctttc tggaggaggg cccggaagaa aacagtgcct atgagcagtt gctgtctcgc    1320
ttggaagaaa tcgctgagga aggctcagag actcaggtcc caggactgga catatctgca    1380
ctcctgccct ctgacttcag ccgctacttc caatatgagg ggtctctgac tacaccgccc    1440
tgtgcccagg tgtcatctg gactgtgttt aaccagacag tgatgctgag tgctaagcag    1500
ctccacaccc tctctgacac cctgtgggga cctggtgact ctcggctaca gctgaacttc    1560
cgagcgacgc agcctttgaa tgggcgagtg attgaggcct ccttccctgc tggagtggac    1620
agcagtcctc gggctgctga gccagtccag ctgaattcct gcctggctgc tggtgacatc    1680
ctagccctgg ttttttggcct cctttttgct gtcaccagcg tcgcgttcct tgtgcagatg    1740
agaaggcagc acagaagggg aaccaaaggg ggtgtgagct accgcccagc agaggtagcc    1800
gagactggag cctagatggt gatggtgatg gtg                                  1833
```

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence:synthetic
      Gly-4SerGly-5Ser flexible peptide linker

<400> SEQUENCE: 3

Gly Gly Gly Gly Ser Gly Gly Gly Gly Gly Ser
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence:synthetic
      four (Ala Gly Ser) flexible peptide linker

<400> SEQUENCE: 4

Ala Gly Ser Ala Gly Ser Ala Gly Ser Ala Gly Ser
1               5                   10

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:synthetic
      PCR first primer with 5' GM-CSF Eco RI

<400> SEQUENCE: 5
gcgggaattc atgtggctgc agagc                                           25

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:synthetic
      PCR second primer with 3' GM-CSF Not I

<400> SEQUENCE: 6

```
gagggaggcg gccgcctcct ggactggctc                                    30
```

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:synthetic
     PCR primer 5' G250 (NotI)

<400> SEQUENCE: 7

```
gagggagcgg ccgctcccct gtgcccc                                       27
```

<210> SEQ ID NO 8
<211> LENGTH: 58
<212> TYPE: DNA
<213> ORGANISM: Artificial Sequence
<220> FEATURE:
<223> OTHER INFORMATION: Description of Artificial Sequence:synthetic
     PCR primer 3' G250-His-stop codon-Bgl II (1)

<400> SEQUENCE: 8

```
gcagaggtag agatctctaa tggtgatggt gatggtgggc tccagtctcg gctacctc     58
```

<210> SEQ ID NO 9
<211> LENGTH: 59
<212> TYPE: DNA
<213> ORGANISM: Artificial Sequence
<220> FEATURE:
<223> OTHER INFORMATION: Description of Artificial Sequence:synthetic
     PCR primer 3' G250-His-stop codon-Bgl II (2)

<400> SEQUENCE: 9

```
ggagagatct ctaatgatga tgatgatgat gatgatgggc tccagtctcg gctacctct    59
```

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:synthetic
     fragment ligation primer rest of Gm-CSF-G250

<400> SEQUENCE: 10

```
gagggcggcc gctcccctgt gcccc                                         25
```

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:synthetic
     beta-actin oligonucleotide amplification primer

<400> SEQUENCE: 11

```
caactccatc atgaagtgtg ac                                            22
```

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:synthetic
     beta-actin oligonucleotide amplification primer

<400> SEQUENCE: 12

```
ctcgcgttca tgaggcacac c                                             21
```

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:synthetic
      GM-CSF oligonucleotide amplification primer

<400> SEQUENCE: 13
ccatgatggc cagccactac                                                       20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:synthetic
      GM-CSF oligonucleotide amplification primer

<400> SEQUENCE: 14
cgacgagaga gtactttgtt c                                                     21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:synthetic
      TNF-alpha oligonucleotide amplification primer

<400> SEQUENCE: 15
tctcgaaccc cgagtgacaa                                                       20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:synthetic
      TNF-alpha oligonucleotide amplification primer

<400> SEQUENCE: 16
ctacattagg aacggcagca t                                                     21

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence:synthetic
      IFN-gamma oligonucleotide amplification primer

<400> SEQUENCE: 17
atgaaatata caagttatat cttggctttt                                            29

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:synthetic
      IFN-gamma oligonucleotide amplification primer

<400> SEQUENCE: 18
tacgacaaag ctccagcttc tcgta                                                 25

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence:synthetic
    IL-2 oligonucleotide amplification primer

<400> SEQUENCE: 19
ggaattaata attacaagaa tccc                                            24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence:synthetic
    IL-2 oligonucleotide amplification primer

<400> SEQUENCE: 20
gaccttgatt tccctagac tttg                                             24

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:synthetic
    IL-4 oligonucleotide amplification primer

<400> SEQUENCE: 21
cttccccctc tgttcttcct                                                 20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:synthetic
    IL-4 oligonucleotide amplification primer

<400> SEQUENCE: 22
gactttgccg agctgtcctt                                                 20

<210> SEQ ID NO 23
<211> LENGTH: 1552
<212> TYPE: DNA
<213> ORGANISM: Homo sapiens
<220> FEATURE:
<221> NAME/KEY: misc_feature
<222> LOCATION: (1)..(1552)
<223> OTHER INFORMATION: G250 kidney tumor specific antigen

<400> SEQUENCE: 23
gcccgtacac accgtgtgct gggacacccc acagtcagcc gcatggctcc cctgtgcccc      60 agccctggc tccctctgtt gatcccggcc cctgctccag gcctcactgt gcaactgctg     120
ctgtcactgc tgcttctgat gcctgtccat ccccagaggt tgccccggat gcaggaggat     180
tcccccttgg gaggaggctc ttctggggaa gatgacccac tgggcgagga ggatctgccc     240
agtgaagagg attcacccag agaggaggat ccacccggag aggaggatct acctggagag     300
gaggatctac ctggagagga ggatctacct gaagttaagc ctaaatcaga agaagggc       360 tccctgaagt tagaggatct acctactgtt gaggctcctg gagatcctca agaacccag     420 aataatgccc acaggggacaa agaaggggat gaccagagtc attggcgcta tggaggcgac     480

```
ccgccctggc cccgggtgtc cccagcctgc gcgggccgct tccagtcccc ggtggatatc      540
cgcccccagc tcgccgcctt ctgcccggcc ctgcgcccc  tggaactcct gggcttccag      600
ctcccgccgc tcccagaact gcgcctgcgc aacaatggcc acagtgtgca actgaccctg      660
cctcctgggc tagagatggc tctggtcccc gggcggagt  accgggctct gcagctgcat      720
ctgcactggg gggctgcagg tcgtccgggc tcggagcaca ctgtggaagg ccaccgtttc      780
cctgccgaga tccacgtggt tcacctcagc accgcctttg ccagagttga cgaggccttg      840
gggcgcccgg gaggcctggc cgtgttggcc gcctttctgg aggagggccc ggaagaaaac      900
agtgcctatg agcagttgct gtctcgcttg aagaaatcg  ctgaggaagg ctcagagact      960
caggtcccag gactggacat atctgcactc ctgccctctg acttcagccg ctacttccaa     1020
tatgaggggt ctctgactac accgccctgt gccagggtg  tcatctggac tgtgtttaac     1080
cagacagtga tgctgagtgc taagcagctc cacaccctct ctgacaccct gtggggacct     1140
ggtgactctc ggctacagct gaacttccga gcgacgcagc ctttgaatgg gcgagtgatt     1200
gaggcctcct tccctgctgg agtggacagc agtcctcggg ctgctgagcc agtccagctg     1260
aattcctgcc tggctgctgg tgacatccta gccctggttt ttggcctcct ttttgctgtc     1320
accagcgtcg cgttccttgt gcagatgaga aggcagcaca aaggggaac  caaaggggggt    1380 gtgagctacc gcccagcaga ggtagccgag actggagcct agaggctgga tcttggagaa     1440
tgtgagaagc cagccagagg catctgaggg ggagccggta actgtcctgt cctgctcatt     1500
atgccacttc cttttaactg ccaagaaatt ttttaaaata aatatttata at             1552
```

<210> SEQ ID NO 24
<211> LENGTH: 763
<212> TYPE: DNA
<213> ORGANISM: Homo sapiens
<220> FEATURE:
<221> NAME/KEY: misc_feature
<222> LOCATION: (1)..(763)
<223> OTHER INFORMATION: human granulocyte macrophage colony stimulating
      factor (GM-CSF)

<400> SEQUENCE: 24

```
taaagttctc tggaggatgt ggctgcagag cctgctgctc ttgggcactg tggcctgcag       60
catctctgca cccgcccgct cgcccagccc cagcacgcag ccctgggagc atgtgaatgc      120
catccaggag gcccggcgtc tcctgaacct gagtagagac actgctgctg agatgaatga     180
aacagtagaa gtcatctcag aaatgtttga cctccaggag ccgacctgcc tacagacccg      240
cctggagctg tacaagcagg gcctgcgggg cagcctcacc aagctcaagg gccccttgac     300
catgatggcc agccactaca agcagcactg ccctccaacc ccggaaactt cctgtgcaac     360
ccagattatc acctttgaaa gtttcaaaga gaacctgaag gactttctgc ttgtcatccc     420
ctttgactgc tgggagccag tccaggagtg agaccggcca gatgaggctg gccaagccgg     480
ggagctgctc tctcatgaaa caagagctag aaactcagga tggtcatctt ggagggacca     540
aggggtgggc cacagccatg gtgggagtgg cctggacctg ccctgggcac actgaccctg     600
atacaggcat ggcagaagaa tgggaatatt ttatactgac agaaatcagt aatatttata     660
tatttatatt tttaaaatat ttatttattt attttatttaa gttcatattc catatttatt     720
caagatgttt taccgtaata attattatta aaaatagctt cta                       763
```

<210> SEQ ID NO 25
<211> LENGTH: 604

```
<212> TYPE: PRT
<213> ORGANISM: Artificial Sequence
<220> FEATURE:
<223> OTHER INFORMATION: Description of Artificial Sequence:G250-GM-CSF
      fusion protein, fusion protein expressed by GM-CSF gene fragment
      (Accession #E02287) linked to G250 gene sequence (Accession
      #X66839) through 6 nucleotides coding for Arg

<400> SEQUENCE: 25
```

Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
                35                  40                  45

Thr Ala Ala Glu Met Asn Glu Thr Val Glu Val Ile Ser Glu Met Phe
50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
130                 135                 140

Arg Arg Ala Pro Leu Cys Pro Ser Pro Trp Leu Pro Leu Leu Ile Pro
145                 150                 155                 160

Ala Pro Ala Pro Gly Leu Thr Val Gln Leu Leu Leu Ser Leu Leu Leu
                165                 170                 175

Leu Met Pro Val His Pro Gln Arg Leu Pro Arg Met Gln Glu Asp Ser
            180                 185                 190

Pro Leu Gly Gly Gly Ser Ser Gly Glu Asp Pro Leu Gly Glu Glu
        195                 200                 205

Asp Leu Pro Ser Glu Glu Asp Ser Pro Arg Glu Glu Asp Pro Pro Gly
    210                 215                 220

Glu Glu Asp Leu Pro Gly Glu Glu Asp Leu Pro Gly Glu Glu Asp Leu
225                 230                 235                 240

Pro Glu Val Lys Pro Lys Ser Glu Glu Glu Gly Ser Leu Lys Leu Glu
                245                 250                 255

Asp Leu Pro Thr Val Glu Ala Pro Gly Asp Pro Gln Glu Pro Gln Asn
            260                 265                 270

Asn Ala His Arg Asp Lys Glu Gly Asp Asp Gln Ser His Trp Arg Tyr
        275                 280                 285

Gly Gly Asp Pro Pro Trp Pro Arg Val Ser Pro Ala Cys Ala Gly Arg
290                 295                 300

Phe Gln Ser Pro Val Asp Ile Arg Pro Gln Leu Ala Ala Phe Cys Pro
305                 310                 315                 320

Ala Leu Arg Pro Leu Glu Leu Leu Gly Phe Gln Leu Pro Pro Leu Pro
                325                 330                 335

Glu Leu Arg Leu Arg Asn Asn Gly His Ser Val Gln Leu Thr Leu Pro
            340                 345                 350

Pro Gly Leu Glu Met Ala Leu Gly Pro Gly Arg Glu Tyr Arg Ala Leu
        355                 360                 365

Gln Leu His Leu His Trp Gly Ala Ala Gly Arg Pro Gly Ser Glu His
    370                 375                 380

Thr Val Glu Gly His Arg Phe Pro Ala Glu Ile His Val Val His Leu
385                 390                 395                 400

Ser Thr Ala Phe Ala Arg Val Asp Glu Ala Leu Gly Arg Pro Gly Gly
                405                 410                 415

Leu Ala Val Leu Ala Ala Phe Leu Glu Glu Gly Pro Glu Glu Asn Ser
            420                 425                 430

Ala Tyr Glu Gln Leu Leu Ser Arg Leu Glu Glu Ile Ala Glu Glu Gly
        435                 440                 445

Ser Glu Thr Gln Val Pro Gly Leu Asp Ile Ser Ala Leu Leu Pro Ser
    450                 455                 460

Asp Phe Ser Arg Tyr Phe Gln Tyr Glu Gly Ser Leu Thr Thr Pro Pro
465                 470                 475                 480

Cys Ala Gln Gly Val Ile Trp Thr Val Phe Asn Gln Thr Val Met Leu
                485                 490                 495

Ser Ala Lys Gln Leu His Thr Leu Ser Asp Thr Leu Trp Gly Pro Gly
            500                 505                 510

Asp Ser Arg Leu Gln Leu Asn Phe Arg Ala Thr Gln Pro Leu Asn Gly
        515                 520                 525

Arg Val Ile Glu Ala Ser Phe Pro Ala Gly Val Asp Ser Ser Pro Arg
    530                 535                 540

Ala Ala Glu Pro Val Gln Leu Asn Ser Cys Leu Ala Ala Gly Asp Ile
545                 550                 555                 560

Leu Ala Leu Val Phe Gly Leu Leu Phe Ala Val Thr Ser Val Ala Phe
                565                 570                 575

Leu Val Gln Met Arg Arg Gln His Arg Arg Gly Thr Lys Gly Gly Val
            580                 585                 590

Ser Tyr Arg Pro Ala Glu Val Ala Glu Thr Gly Ala
        595                 600

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence:synthetic
      His-6 tag

<400> SEQUENCE: 26

His His His His His His
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence:synthetic
      8 His

<400> SEQUENCE: 27

His His His His His His His His
1               5

KIDNEY-SPECIFIC TUMOR VACCINE DIRECTED AGAINST KIDNEY TUMOR ANTIGEN G-250

CROSS-REFERENCE TO RELATED APPLICATIONS

This application is a divisional of a U.S. application Ser. No. 14/268,662, filed on May 2, 2014, which is a continuation of U.S. application Ser. No. 12/479,415, filed on Jun. 5, 2009, issued as U.S. Pat. No. 8,741,306, which is a divisional of U.S. application Ser. No. 09/783,708, filed on Feb. 13, 2001, issued as U.S. Pat. No. 7,572,891, which claims benefit of U.S. provisional applications U.S. Ser. No. 60/182,429, filed on Feb. 14, 2000, and U.S. Ser. No. 60/182,636, filed on Feb. 15, 2000, each of which are incorporated herein by reference in their entirety for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file—079822-1010210_SequenceListing.txt, created on Jun. 8, 2016, 23,375 bytes, machine format IBM-PC, MS-Windows operating system, is hereby incorporated by reference in its entirety for all purposes.

FIELD OF THE INVENTION

This invention relates to the field of oncology. In particular this invention provides novel vaccines for use in the treatment of renal cell cancers.

BACKGROUND OF THE INVENTION

Renal cell carcinoma (RCC), also often identified as renal cancer, "hypernephroma", or adenocarcinoma of the kidney accounts for about 85 percent of all primary renal neoplasms. Approximately 25,000 new cases are diagnosed annually with 10,000 deaths in the United States. Unfortunately, the prognosis of patients with recurrent or metastatic renal cell carcinoma remains poor. Chemotherapy and radiotherapy have little or no activity in this disease and there is no standard chemotherapeutic, hormonal, or immunologic program for recurrent or metastatic renal cancer.

Commonly employed chemotherapy programs include the use of vinblastine sulfate, with or without the use of nitrosoureas. Interferons have been used with very limited success. Interleukin 2 (Aldesleukin) is approved for treatment of selected patients with metastatic renal cell carcinoma. An overall response rate of 15 percent has been noted in 255 patients, but this has been accompanied by both severe adverse reactions and a few treatment-related deaths. Other treatment options for patients with advanced disease are, at best, investigational.

SUMMARY OF THE INVENTION

This invention provides a novel approach to the treatment of renal cell carcinomas. In particular this invention pertains to the discovery that a chimeric molecule comprising a granulocyte macrophage colony stimulating factor (GM-CSF) attached to a G250 kidney cancer specific antigen provides a highly effective "vaccine" that raises an immune response directed against renal cell cancers. The chimeric molecule can be used as a traditional vaccine or in adoptive immunotherapeutic applications. Nucleic acids encoding a GM-CSF-G250 fusion protein can be used as naked DNA vaccines or to transfect cell in an adoptive immunotherapeutic treatment regimen.

Thus in one embodiment, this invention provides a construct comprising a G250 kidney cancer specific antigen attached to a granulocyte macrophage colony stimulating factor (GM-CSF). The GM-CSF is preferably a human GM-CSF, or a biologically active fragment and/or mutant thereof. Similarly the G250 antigen is a preferably a human G250 antigen. In particularly preferred embodiments the G250 antigen is covalently attached to the GM-CSF (directly or through a linker). Preferred linkers are encoded by the nucleotide sequence gcggcg. In a particularly preferred embodiment the G250 antigen and the GM-CSF are components of a fusion protein (chemically constructed or recombinantly expressed). In such fusion proteins, the G250 antigen and the GM-CSF are directly joined, or more preferably, joined by a peptide linker ranging in length from 2 to about 50, more preferably from about 2 to about 20, and most preferably from about 2 to about 10 amino acids. One preferred peptide linker is -Arg-Arg-. A particularly preferred embodiment has the sequence of SEQ ID NO: 1 (excluding the $His_6$ (SEQ ID NO:26) tag).

In another embodiment this invention provides a composition comprising the chimeric molecules described herein and a pharmaceutically acceptable diluent or excipient.

This invention also provides a nucleic acid (e.g. a DNA or an RNA) encoding a fusion protein comprising a G250 kidney cancer specific antigen attached to a granulocyte macrophage colony stimulating factor (GM-CSF). The G250 is preferably a human G250 (or an antigenic fragment or cancer-specific epitope thereof). Similarly the GM-CSF is a preferably a human GM-CSF or a biologically active fragment thereof. In one preferred embodiment the nucleic acid encodes a fusion protein where the G250 antigen and the GM-CSF are directly joined, or more preferably, joined by a peptide linker ranging in length from 2 to about 50, more preferably from about 2 to about 20, and most preferably from about 2 to about 10 amino acids. In certain embodiments, the nucleic acid may preferably encode a linker that is -Arg-Arg-. One preferred nucleic acid is the nucleic acid of SEQ ID NO: 2. In some preferred embodiments, the nucleic acid is a nucleic acid that encodes the polypeptide of SEQ ID NO: 1. The nucleic acid is preferably in an expression cassette and in certain embodiments, the nucleic acid is present in a vector (e.g. a baculoviral vector).

This invention also provides a host cell transfected with one or more of the nucleic acids described herein. The host cell is preferably a eukaryotic cell, and most preferably an insect cell.

This invention also provides methods of producing an anti-tumor vaccine. The methods preferably involve culturing a cell transfected with a nucleic acid encoding a chimeric GM-CSF-G250 chimeric molecule under conditions where the nucleic acid expresses a G250-GM-CSF fusion protein and recovering said fusion protein. Again the cell is preferably a eukaryotic cell, more preferably an insect (e.g. an SF9) cell.

In another embodiment, this invention provides methods of inducing an immune response against the G250 kidney-specific antigen, and/or a cell displaying the G250 kidney-specific antigen, and/or any cancer cell that expresses a G250 antigen, and/or an antigen cross-reactive with a G250 antigen. The methods involve activating a cell of the immune system with a construct comprising a kidney cancer specific antigen (G250) attached to a granulocyte macrophage colony stimulating factor (GM-CSF) whereby the activating provides an immune response directed against the G250 antigen. In some embodiments, the activating comprises contacting an antigen presenting cell (e.g. monocyte, or dendritic cell) with the construct (chimeric molecule). In certain embodiments, the activated cell is a cytotoxic T-lymphocyte (CTL), or a tumor infiltrating lymphocyte, etc. The activating can also involve contacting a peripheral blood lymphocyte (PBL) or a tumor infiltrating lymphocyte (TIL) with the construct. The contacting can take place in vivo, or ex vivo (e.g., in vitro). In various embodiments, the activating comprises loading an antigen presenting cell (APC) with a polypeptide comprising a G250. The activation can also comprise transfecting a cell (e.g., a PBL, an APC, a TIL, a renal cell carcinoma tumor cell, etc.) with a nucleic acid encoding a GM-CSF-G250 fusion protein. The method may further comprise infusing cells (e.g. cytotoxic T lymphocytes) back into the mammal.

In still another embodiment this invention provides a method of inhibiting the proliferation or growth of a transformed (e.g. neoplastic) kidney cell. The method involves activating a cell of the immune system with a construct comprising a kidney cancer specific antigen (G250) attached to a granulocyte macrophage colony stimulating factor (GM-CSF) whereby the activating provides an immune response directed against the G250 antigen and the immune response inhibits the growth or proliferation of a transformed kidney cell. In preferred embodiments, the transformed kidney cell is a renal cell carcinoma cell (e.g. in a solid tumor, a disperse tumor, or a metastatic cell). The activating can comprise contacting an antigen presenting cell (e.g. a dendritic cell) with the construct. The activated cell can include, but is not limited to a cytotoxic T-lymphocyte (CTL) a tumor infiltrating lymphocyte (TIL), etc. In certain embodiments, the activating comprises injecting (or otherwise administering) to a mammal one or more of the following: a polypeptide comprising a GM-CSF-G250 fusion protein; dendritic cells pulsed with a GM-CSF-G250 fusion protein; a gene therapy construct (e.g. adenovirus, gutless-adenovirus, retrovirus, lentivirus, adeno-associated virus, vaccinia virus, etc) comprising a nucleic acid encoding a GM-CSF-G250 fusion protein, a dendritic expressing a GM-CSF-G250 fusion protein, a tumor cell (e.g. RCC) expressing a GM-CSF-G250 fusion protein, a fibroblast expressing a GM-CSF-G250 fusion protein, a GM-CSF-G250 naked DNA, a transfection reagent (e.g. cationic lipid, dendrimer, liposome, etc. containing or complexed with a nucleic acid encoding a GM-CSF-G250 polypeptide. In a particularly preferred embodiment, activating comprises activating isolated dendritic cells/PMBCs. In another embodiment, the activating comprises contacting (in vivo or ex vivo) a peripheral blood lymphocyte (PBL) or a tumor infiltrating lymphocyte (TEL) with said construct. The peripheral blood cells and/or dendritic cells and/or monocytes are preferably infused into the subject.

This invention also provides a method of inhibiting the proliferation or growth of a transformed renal cell that bears a G250 antigen. The method involves removing an immune cell from a mammalian host; activating the immune cell by contacting the cell with a protein comprising a renal cell carcinoma specific antigen (G250) attached to a granulocyte macrophage colony stimulating factor (GM-CSF) or a fragment thereof; optionally expanding the activated cell; and infusing the activated cell into an organism containing a transformed renal cell bearing a G250 antigen. In certain embodiments, the activating comprises contacting the cell with one or more of the following: a polypeptide comprising a GM-CSF-G250 fusion protein; dendritic cells pulsed with a GM-CSF-G250 fusion protein; a gene therapy construct (e.g. adenovirus, gutless-adenovirus, retrovirus, lantivirus, adeno-associated virus, vaccinia virus, etc) comprising a nucleic acid encoding a GM-CSF-G250 fusion protein, a dendritic expressing a GM-CSF-G250 fusion protein, a tumor cell (e.g. RCC) expressing a GM-CSF-G250 fusion protein, a fibroblast expressing a GM-CSF-G250 fusion protein, a GM-CSF-G250 naked DNA, a transfection reagent (e.g. cationic lipid, dendrimer, liposome, etc. containing or complexed with a nucleic acid encoding a GM-CSF-G250 polypeptide. In a particularly preferred embodiment, activating comprises activating isolated dendritic cells/PMBCs. In another embodiment, the activating comprises contacting (in vivo or ex vivo) a peripheral blood lymphocyte (PBL) or a tumor infiltrating lymphocyte (TIL) with said construct. The peripheral blood cells and/or dendritic cells and/or monocytes are preferably infused into the subject. The removing may comprise isolating and culturing peripheral blood lymphocytes and/or monocytes, and/or dendritic cells from the mammalian host. The infusing may involve infusing the cultured cells or activated cells produced using the cultured cells into the host from which the immune cell was removed.

In still another embodiment, this invention provides a method of treating an individual having a renal cell cancer. The method involves sensitizing antigen presenting cells (e.g., PBMCs, dendritic cells, etc.) in vitro with a sensitizing-effective amount of a chimeric fusion protein comprising a renal cell carcinoma specific antigen (G250) attached to a granulocyte macrophage colony stimulating factor (GM-CSF); and administering to an individual having said renal cell cancer or metastasis a therapeutically effective amount of the sensitized antigen presenting cells. In particularly preferred embodiments, the antigen presenting cells are autologous to the individual or allogenic with matched MHC. In certain embodiments, the sensitizing involves contacting peripheral blood lymphocytes or monocytes or dendritic cells with G250-GM-CSF fusion protein. In certain embodiments, the sensitizing involves contacting PBL, TIL, monocyte, dendritic cell with a G250-GM-CSF polypeptide and/or transfecting dendritic cell, APC, RCC, fibroblasts, with a nucleic acid encoding the chimeric fusion protein.

Definitions

The term "G250-GM-CSF" refers to a chimeric molecule comprising a G250 renal cell tumor antigen attached to a granulocyte-macrophage colony stimulating factor. The attachment may be a chemical conjugation (direct or through a linker) or the chimeric molecule can be a fusion protein (recombinantly expressed or assembled by condensation of the two subject molecules). The notation "G250-GM-CSF" encompasses embodiments where the G250 and the GM-CSF are attached terminally or to an internal site and contemplates attachment of the G250 molecule to either the amino or carboxyl terminus of the GM-CSF. In addition, the term my encompass chimeric molecules comprising fragments or mutants of G250 where the G250 fragments retain the epitope recognized by antibodies that specifically target renal cell carcinomas bearing the G250 antigen. Similarly, the term my encompass chimeric molecules comprising fragments or mutants of GM-CSF where the GM-CSF retain the biological activity of native GM-CSF (e.g. are recognized by receptors that recognize native GM-CSF and/or show similar mitogenic activity, etc.)

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19: 1437; and U.S. Pat. No. 5,644,048), phosphorodithioate (Briu et al. (1989) *J. Am. Chem. Soc.* 111: 2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114: 1895; Meier et al. (1992) *Chem. Int. Ed. Engl.* 31: 1008; Nielsen (1993) *Nature*, 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110: 4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "immune cell" refers to a cell that is capable of participating, directly or indirectly, in an immune response. Immune cells include, but are not limited to T-cells, B-cells, dendritic cells, cytotoxic T-cells, tumor infiltrating lymphocytes, etc.

As used herein, the term "activating" (e.g. as in activating a cell or activating an immune response) includes direct activation as by contact with the construct or by indirect activation as by contact with the construct or antigenic fragment via an antigen presenting cell (e.g. a dendritic cell).

A "fusion protein" refers to a polypeptide formed by the joining of two or more polypeptides through a peptide bond formed between the amino terminus of one polypeptide and the carboxyl terminus of another polypeptide. The fusion protein may be formed by the chemical coupling of the constituent polypeptides, or it may be expressed as a single polypeptide from nucleic acid sequence encoding the single contiguous fusion protein. A single chain fusion protein is a fusion protein having a single contiguous polypeptide backbone.

A "spacer" or "linker" as used in reference to a fusion protein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

A "spacer" or "linker" as used in reference to a chemically conjugated chimeric molecule refers to any molecule that links/joins the constituent molecules of the chemically conjugated chimeric molecule.

BRIEF DESCRIPTION OF THE DRAWINGS

FIG. 4 illustrates cytotoxicity of bulk PMBC modulated by G250-GM-CSF fusion protein (patient 1).

FIG. 5 illustrates cytotoxicity of bulk PBMC modulated by GM-cSF/G250 fusion protein (patient 2).

FIGS. 6A, 6B and 6C illustrate the expression and purification of GM-CSF-G250 fusion protein. FIG. 6A shows immunohistochemical staining for G250 and GM-CSF expression with anti-G250 and anti-GM-CSF antibodies Sf-9 cells infected with and without fusion gene recombinant baculovirus. Magnification, ×100. FIG. 6B shows a Western blot analysis of 6×His-tagged GM-CSF-G250 fusion protein eluted from the Ni-NTA affinity column using antiGM-CSF antibody (L=loading, BT=break through, W=wash). FIG. 6C shows a coomassive blue-stained SDS-PAGE of fusion protein eluted from Ni-NTA affinity column (lane 1) and further purified with SP Sepharose/FPLC (lane 2 and lane 3).

FIG. 8A shows a double-color flow cytometric analysis of dendritic cells grown in GM-CSF (800 U/ml) plus IL-4 (1000 U/ml) or fusion protein (FP) plus IL-4. Cells were labeled with FITC and PE conjugated antibodies against cell surface markers of DC, as indicated. Cells that were larger than lymphocytes were selectively gated and negative controls correspond to labeling with an isotype-matched control antibody. This analysis is representative of 5 DC cultures. FIG. 8B shows a flow cytometric analysis of HLA antigens of DC cultured in GM-CSF plus IL-4 or Fusion protein plus IL-4. Cells labeled with primary antibody (HLA class I or class II) and FITC-conjugated secondary antibody. This analysis is representative of four different DC derived from four RCC patients. FIG. 8C shows a double-color flow cytometric analysis of DC expressed CD83$^+$ CD19$^-$ that cultured in the condition as indicated. Data, means of triplicate; bars, SD. This analysis is representative of four different DC derived from four RCC patients.

FIG. 10A shows growth expansion of PBMC (patient #1) induced by various immunomodulatory strategies as indicated. Cell cultures were stimulated with FP on day 0, day 6, day 12 and day 18. Culture medium was changed weekly but maintained in a constant volume. Cell counts were performed on day 20. Expansion fold was calculated by division of final cell counts per ml with cell counts per ml seeded on day 0 (3×105 cells/ml). Data, means of triplicate; bars, SD. This analysis is representative of four different PBMC cultures derived from four RCC patients, which showed a similar growth profile. FIG. 10B shows cytotoxicity of PBMC (patient #1) against autologous normal kidney cells, primary tumor cells and lymph node derived tumor cells. Cytotoxicity was determined by 18-h 51Cr-release assay on day 21. Killing activity was expressed as the lytic units per 106 effector cells. Lytic units are defined as the number of effector cells capable of inducing 30% lysis. Spontaneous release for tumor target was <20% of maximal release. Data, means of triplicate; bars, SD. FIG. 10C shows the inhibition of cytotoxicity against autologous LN tumor cells by antibodies specific to T cells and FLA antigens. Tumor target cells or PBMC were pretreated with respective antibody as indicated prior to cytotoxicity assay. Data, means of triplicate; bars, SD. FIG. 10D: Semi-quantitative RT-PCR analysis of G250 mRNA expression by normal kidney, primary tumor and LN derived tumor derived from patient #1.

FIG. 11A shows cytotoxicity of PBMC against autologous and allogenic tumor targets as indicated. PBMC cultures were pretreated with IL-4 (1000 U/ml) and FP (0.34 mg/ml) or IL-4 and GM-CSF (800 U/mi) for one week and then restimulated with IL-2 and FP or IL-2 and GM-CSF weekly. Cytotoxicity was determined by 18-h 51Cr-release assay on day 35. Cytotoxicity against autologous tumor target was measured in the presence of isotype control antibody or antibodies specific to HLA class I, HLA class II, CD3, CD4, or CD8. Data, means of triplicate; bars, SD. FIG. 11B shows a phenotypic analysis of FP modulated PBMC that expressed antitumor activity.

DETAILED DESCRIPTION

Figure 1:
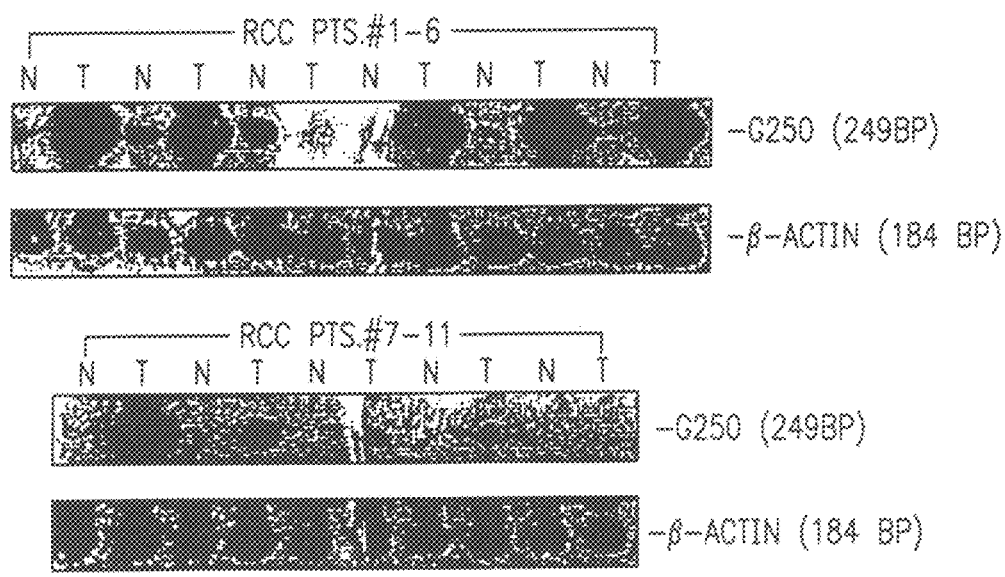
FIG. 1 illustrates a RT-PCR analysis of RCC tumor cells.

This invention provides a novel approach to the treatment (e.g. mitigation of symptoms) of a renal cell carcinoma or any type of cancer that expresses G250 antigen (e.g. cervical cancer) or that expresses an antigen cross-reactive with G250. In particular this invention utilizes a chimeric molecule comprising a kidney cancer specific antigen (G250) attached to a granulocyte-macrophage colony stimulating factor (GM-CSF). Without being bound to a particular theory, it is believed that this chimeric molecule affords two modes of activity. Vaccination of patients with advanced renal cell carcinoma using a chimeric G250-GM-CSF molecule will result in activation of the patient's dendritic cells (DC), the most potent antigen presenting cells. The dendritic cells take up GM-CSF, e.g., via the GM-CSF receptor and the attached G250 antigen is co-transported by virtue of its attachment to the GM-CSF. The dendritic cells process the G250 antigen and present G250 peptide on HLA class I which then activates G250 specific cytotoxic T cells (CD3$^+$ CD8$^+$) which can then lyse G250 positive kidney cancer cells. In addition, or alternatively, the G250 peptide is presented on HLA class II cells that activate G250 specific T helper cells which then activate or maintain the killing activity of CTLs.

In certain embodiments, a nucleic acid encoding a G250-GM-CSF construct can be administered as a "naked DNA" vaccine. In this approach, the organism/patient is injected, e.g. intramuscularly, with a nucleic acid encoding a G250-GM-CSF fusion protein. The nucleic acid is expressed within the organism leading to the production of a G250-GM-CSF fusion protein which then elicits an anti-renal cell carcinoma immune response as described above.

In another embodiment, the chimeric G250-GM-CSF molecules can be used in adoptive immunotherapy. In this instance, the chimeric molecule (fusion protein) or a nucleic acid encoding the chimeric molecule is used to activate lymphocytes (e.g. T-cells) ex vivo. The activated lymphocytes are optionally expanded, ex vivo, and then re-infused back into the subject (patient) where they specifically attack and lyse G250 positive tumor cells (e.g. kidney cells tumor or cervical cancer cells).

In particularly preferred embodiments, this invention utilizes one or more of the following formulations:
1. A polypeptide comprising a GM-CSF-G250 fusion protein
2. Dendritic, or other cells, pulsed with a polypeptide comprising a GM-CSF-G250 fusion protein;
3. GM-CSF-G250 encoding nucleic acids in a "gene therapy" vector (e.g. adenovirus, gutless-adenovirus, retrovirus, lantivirus, adeno-associated virus, vaccinia virus, etc.)
4. Dendritic cells transfected with a GM-CSF-G250-encoding nucleic acid (e.g., via recombinant virus, plasmid DNA transfection, and the like);
5. Tumor cells (e.g. RCC cells) comprising a nucleic acid encoding a polypeptide comprising a GM-CSF-G250 fusion protein;

7. A nucleic acid encoding a GM-CSF-G250 (e.g. "naked DNA"); and
8. A nucleic acid encoding a polypeptide comprising a GM-CSF-G250 complexed with a transfection agent (e.g., DMRIE/DOPE lipid, dendrimers, etc.)

Each of these formulations can be directly administered to an organism (e.g. a mammal having a cancer that expresses a G250 antigen or an antigen cross-reactive to a G250 antigen) or can be used in an adoptive immunotherapy context. In the latter approach, the adoptive immunotherapy preferably utilizes cells derived from peripheral blood (e.g. peripheral blood lymphocytes (PBLs) or cells derived from a tumor (e.g. tumor infiltrating lymphocytes (TILs)). Administration of the formulation results in activation and propagation of G250-targeted cytotoxic T cells in PBMC or TIL cultures. Infusion of the G250-targeted CTLs into the patient results in the development and maintenance of a G250-directed immune response.

The formulations identified above can also be administered directly to a mammal for "in vivo" vaccination. Thus, for example, GM-CSF-G250 polypeptides or nucleic acids endoding such polypeptides can be administered to the organism as "traditional" vaccines. The other immunogenic formulations identified above, however, are also highly active in vivo and can also be "directly" administered to an organism as a "vaccine". Thus, for example, dendritic cells pulsed with a GM-CSF-G250 fusion protein, dendritic, or other cells, transfected with a nucleic acid encoding a GM-CSF-G250 fusion protein, gene therapy vectors encoding a GM-CSF-G250 polypeptide, can all be administered to an organism where they induce and maintain a population of G250-directed cytotoxic T cells.

It was a discovery of this invention that the G250-GM-CSF chimeric molecules e.g. when used in vivo as a vaccine or in an adoptive immunotherapeutic modality induce a highly vigorous immune response specifically directed at renal cell carcinomas. The approach results in the death or inhibition of neoplastic renal cells whether diffuse (e.g. motile metastatic cells) or aggregated (e.g. as in a solid tumor). These methods can accompany administration of other agents (e.g. immunomodulatory or cytotoxic agents, such as cytokines or drugs).

It is recognized that the methods of this invention need not show complete tumor elimination (e.g. a "cure") to be of value. Even a slight decrease in the growth rate of a tumor, and/or in the propagation of metastatic, or other neoplastic, cells can be clinically relevant improving the quality and/or duration of life. Of course, given the high efficacy observed, it is expected that the methods of this invention may offer a significant or complete degree of remission particularly when used in combination with other treatment modalities (e.g. surgery, chemotherapy, interleukin therapy, TGFβ or IL-10 antisense therapy, etc.).

I. G250-GMCSF Chimeric Molecules and their Expression.

This invention utilizes a chimeric molecule comprising a G250 kidney cancer-specific antigen attached to a granulocyte-macrophage colony stimulating factor (GM-CSF) to induce a cell-mediated immune response targeted to renal tumor cells. In a chimeric molecule, two or more molecules that exist separately in their native state are joined together to form a single molecule having the desired functionality of all of its constituent molecules. In this instance, the constituent molecules are the G250 antigen and GM-CSF respectively. The G250 provides an epitope that is presented (e.g. to T-cells) resulting in activation and expansion of those cells and the formation of cytotoxic cells (e.g. cytotoxic T lymphocytes, tumor infiltrating lymphocytes (TILs), etc.) that are direct to tumor cells bearing the G250 antigen. The GM-CSF acts both to stimulate components of the immune system (e.g. monocytes, dendritic cells, NK, PMN, PBMC, etc.) and to mediate uptake of the associated G250 antigen by dendritic cells. In addition, particularly in adoptive immunotherapeutic modalities, the GM-CSF also can act as an adjuvant.

The attachment of the G250 antigen to the GM-CSF can be direct (e.g. a covalent bond) or indirect (e.g. through a linker). In addition, the G250 antigen and the GM-CSF proteins can be attached by chemical modification of the proteins or they can be expressed as a recombinant fusion protein. Detailed methods of producing the individual components and the chimeric molecule are provided below.

The G250 kidney tumor specific antigen is known to those of skill in the art (see, e.g., Oosterwijk et al. (1996) *Molecular characterization of the Renal Cell Carcinoma-associated antigen G250, Proc. Natl. Acad. Sci., USA,* 37: 461; Uemura et al., (1994) *Internal Image Anti-Idiotype Antibodies Related to Renal-Cell Carcinoma-Associated Antigen G250, Int. J Cancer,* 56: 609-614). The G250 nucleic acid sequence is publicly available (see, e.g., GenBank Accession number X66839).

```
Nucleic acid sequence of G250 (SEQ ID NO: 23):
gcccgtacac accgtgtgct gggacacccc acagtcagcc gcatggctcc cctgtgcccc agccctggc tccctctgtt gatcccggcc cctgctccag gcctcactgt gcaactgctg ctgtcactgc tgcttctgat gcctgtccat ccccagaggt tgccccggat gcaggaggat tcccccttgg gaggaggctc ttctggggaa gatgacccac tgggcgagga ggatctgccc agtgaagagg attcacccag agaggaggat ccaccggag aggaggatct acctggagag gaggatctac ctggagagga ggatctacct gaagttaagc ctaaatcaga agaagagggc tccctgaagt tagaggatct acctactgtt gaggctcctg gagatcctca agaacccag aataatgccc acagggacaa agaaggggat gaccagagtc attggcgcta tggaggcgac ccgcctggc cccgggtgtc cccagcctgc gcgggccgct tccagtcccc ggtggatatc cgcccccagc tcgccgcctt ctgcccggcc ctgcgccccc tggaactcct gggcttccag ctccgccgc tcccagaact gcgcctgcgc aacaatggcc acagtgtgca actgacctg cctcctgggc tagagatggc tctgggtccc gggcgggagt accgggctct gcagctgcat
```

```
ctgcactggg gggctgcagg tcgtccgggc tcggagcaca ctgtggaagg ccaccgtttc cctgccgaga tccacgtggt tcacctcagc accgcctttg ccagagttga cgaggccttg gggcgcccgg gaggcctggc cgtgttggcc gcctttctgg aggagggccc ggaagaaaac agtgcctatg agcagttgct gtctcgcttg gaagaaatcg ctgaggaagg ctcagagact caggtcccag gactggacat atctgcactc ctgccctctg acttcagccg ctacttccaa tatgaggggt ctctgactac accgccctgt gcccagggtg tcatctggac tgtgtttaac cagacagtga tgctgagtgc taagcagctc cacaccctct ctgacaccct gtggggacct ggtgactctc ggctacagct gaacttccga gcgacgcagc ctttgaatgg gcgagtgatt gaggcctcct tccctgctgg agtggacagc agtcctcggg ctgctgagcc agtccagctg aattcctgcc tggctgctgg tgacatccta gccctggttt ttggcctcct ttttgctgtc accagcgtcg cgttccttgt gcagatgaga aggcagcaca gaaggggaac caaagggggt gtgagctacc gcccagcaga ggtagccgag actggagcct agaggctgga tcttggagaa tgtgagaagc cagccagagg catctgaggg ggagccggta actgtcctgt cctgctcatt atgccacttc cttttaactg ccaagaaatt ttttaaaata aatatttata at
```

Similarly, the nucleic acid sequence of GM-CSF (e.g. human GM-CSF) is well known to those of skill in the art (see, e.g., GenBank accession no: E02287).

```
Nucleic acid sequence of GM-CSF (SEQ ID NO: 24):
taaagttctc tggaggatgt ggctgcagag cctgctgctc ttgggcactg tggcctgcag catctctgca cccgcccgct cgcccagccc cagcacgcag ccctgggagc atgtgaatgc catccaggag gcccggcgtc tcctgaacct gagtagagac actgctgctg agatgaatga aacagtagaa gtcatctcag aaatgtttga cctccaggag ccgacctgcc tacagacccg cctggagctg tacaagcagg gcctgcgggg cagcctcacc aagctcaagg gcccttgac catgatggcc agccactaca agcagcactg ccctccaacc ccggaaactt cctgtgcaac ccagattatc acctttgaaa gtttcaaaga gaacctgaag gactttctgc ttgtcatccc ctttgactgc tgggagccag tccaggagtg agaccggcca gatgaggctg gccaagccgg ggagctgctc tctcatgaaa caagagctag aaactcagga tggtcatctt ggagggacca aggggtgggc cacagccatg gtgggagtgg cctggacctg ccctgggcac actgaccctg atacaggcat ggcagaagaa tgggaatatt ttatactgac agaaatcagt aatatttata tatttatatt tttaaaatat ttatttattt atttatttaa gttcatattc catatttatt caagatgttt taccgtaata attattatta aaaatagctt cta
```

Using the known sequence information nucleic acids encoding G250, GM-CSF, or a chimeric G250-GM-CSF can be produced using standard methods well known to those of skill in the art. For example, the nucleic acid(s) may be cloned, or amplified by in vitro methods, such as the polymerase chain reaction (PCR), the ligase chain reaction (LCR), the transcription-based amplification system (TAS), the self-sustained sequence replication system (SSR), etc. A wide variety of cloning and in vitro amplification methodologies are well known to persons of skill in the art.

Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning-A Laboratory Manual* (2nd ed.) Vol. 1-3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, *Inc. and* John Wiley & Sons, Inc., (1994 Supplement) (Ausubel); Cashion et al., U.S. Pat. No. 5,017,478; and Carr, European Patent No. 0,246,864.

Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science*, 241: 1077-1080; Van Brunt (1990) *Biotechnology*, 8: 291-294; Wu and Wallace, (1989) *Gene*, 4: 560; and Barringer et al. (1990) *Gene*, 89: 117.

In addition, the cloning and expression of a GM-CSF-G250 fusion gene is described in Example 1. While the cloning and expression of a recombinant fusion protein is illustrated it will be appreciated that the G250 and GM-CSF proteins can be purchased and/or recombinantly expressed and then chemically coupled as described below.

The G250 and the GM-CSF molecules may be joined together in any order. Thus, the G250 can be joined to either the amino or carboxy termini of the GM-CSF. Where the molecules are chemically conjugated, they need not be joined end to end and can be attached at any convenient terminal or internal site.

The G250 and GM-CSF may be attached by any of a number of means well known to those of skill in the art. Typically the G250 and the GM-CSF are conjugated, either directly or through a linker (spacer). Because both molecules are polypeptides, in one embodiment, it is preferable to recombinantly express the chimeric molecule as a single-chain fusion protein that optionally contains a peptide spacer between the GM-CSF and the G250.

Means of chemically conjugating molecules are well known to those of skill. Polypeptides typically contain variety of functional groups; e.g., carboxylic acid (COOH) or free amine (—NH$_2$) groups, which are available for reaction with a suitable functional group on an effector molecule to bind the effector thereto.

Alternatively, the G250 and/or the GM-CSF may be derivatized to expose or attach additional reactive functional groups. The derivatization may involve attachment of any of a number of linker molecules such as those available from Pierce Chemical Company, Rockford Ill.

A "linker", as used herein, is a molecule that is used to join the G250 to the GM-CSF. In preferred embodiments, the linker is capable of forming covalent bonds to both the G250 and GM-CSF. Suitable linkers are well known to those of skill in the art and include, but are not limited to, straight or branched-chain carbon linkers, heterocyclic carbon linkers, or peptide linkers. In certain embodiments, the linkers may be joined to amino acids comprising G250 and/or GM-CSF through their side groups (e.g., through a disulfide linkage to cysteine). However, in a preferred embodiment, the linkers will be joined to the alpha carbon amino and carboxyl groups of the terminal amino acids. The linker may be bifunctional, having one functional group reactive with a substituent on the G250 and a different functional group reactive with a substituent on the GM-CSF. Alternatively, the G250 and/or the GM-CSF may be derivatized to react with a "mono-functional" linker (see, e.g., U.S. Pat. Nos. 4,671,958 and 4,659,839 for procedures to generate reactive groups on peptides).

In a particularly preferred embodiment, the chimeric molecules of this invention are fusion proteins. The fusion protein can be chemically synthesized using standard chemical peptide synthesis techniques, or, more preferably, recombinantly expressed. Where both molecules are relatively short the chimeric molecule may be synthesized as a single contiguous polypeptide. Solid phase synthesis in which the C-terminal amino acid of the sequence is attached to an insoluble support followed by sequential addition of the remaining amino acids in the sequence is a preferred method for the chemical synthesis of the polypeptides of this invention. Techniques for solid phase synthesis are described by Barany and Merrifield, *Solid-Phase Peptide Synthesis; pp.* 3-284 in *The Peptides: Analysis, Synthesis, Biology. Vol. 2: Special Methods in Peptide Synthesis, Part A.*, Merrifield, et al. *J. Am. Chem. Soc.*, 85: 2149-2156 (1963), and Stewart et al., *Solid Phase Peptide Synthesis*, 2nd ed. Pierce Chem. Co., Rockford, Ill. (1984).

In a most preferred embodiment, the chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion protein of this invention (GM-CSF-G250) may be prepared by any suitable method, including, for example, cloning and restriction of appropriate sequences or direct chemical synthesis by methods such as the phosphotriester method of Narang et al. *Meth. Enzymol.* 68: 90-99 (1979); the phosphodiester method of Brown et al., *Meth. Enzymol.* 68: 109-151 (1979); the diethylphosphoramidite method of Beaucage et al., *Tetra. Lett.*, 22: 1859-1862 (1981); and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

In a preferred embodiment, DNA encoding fusion proteins of the present invention is using DNA amplification methods such as polymerase chain reaction (PCR). As illustrated in Examples 1 and 2. Thus, for example, GM-CSF is amplified using primers that introduce EcoRI and NotI sites (3' and 5' respectively), and G250 cDNA is amplified with primers introducing NotI and His-stop-GbL II (5' and 3' respectively). The amplification products are ligated (GM-CSF-NotI-G250-His-stop-Bgl II).

The constructs illustrated in Example 1 introduce a linker (gcggcg) between the nucleic acids encoding G250 and GM-CSF. The linker sequence is used to separate GM-CSF and G250 by a distance sufficient to ensure that, in a preferred embodiment, each domain properly folds into its secondary and tertiary structures. Preferred peptide linker sequences adopt a flexible extended conformation, do not exhibit a propensity for developing an ordered secondary structure that could interact with the functional GM-CSF and G250 domains. Typical amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, also may be used in the linker sequence. Thus, amino acid sequences useful as linkers of GM-CSF and G250, in addition to the one illustrated in Example 1, include the Gly$_4$SerGly$_5$Ser linker (SEQ ID NO:3) used in U.S. Pat. No. 5,108,910 or a series of four (Ala Gly Ser) residues (SEQ ID NO:4), etc. Still other amino acid sequences that may be used as linkers are disclosed in Maratea et al. (1985), *Gene* 40: 39-46; Murphy et al. (1986) *Proc. Nat'l. Acad. Sci. USA* 83: 8258-62; U.S. Pat. No. 4,935,233; and U.S. Pat. No. 4,751,180.

The length of the peptide linker sequence may vary without significantly affecting the biological activity of the fusion protein. In one preferred embodiment of the present invention, a peptide linker sequence length of about 2 amino acids is used to provide a suitable separation of functional protein domains, although longer linker sequences also may be used. The linker sequence may be from 1 to 50 amino acids in length. In the most preferred aspects of the present invention, the linker sequence is from about 1-20 amino acids in length. In the specific embodiments disclosed herein, the linker sequence is from about 2 to about 15 amino acids, and is advantageously from about 2 to about 10 amino acids. Peptide linker sequences not necessarily required in the fusion proteins of this invention.

Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

Where it is desired to recombinantly express either the G250, the GM-CSF, or the G250-GM-CSF fusion protein, the nucleic acid sequences encoding the desired protein are typically operably linked to suitable transcriptional or translational regulatory elements. The regulatory elements typically include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants may additionally be incorporated.

The nucleic acid sequences encoding the fusion proteins may be expressed in a variety of host cells, including E. coli and other bacterial hosts, and eukaryotic host cells including but not limited to yeast, insect cells (e.g. SF9 cells) and various other eukaryotic cells such as the COS, CHO and HeLa cells lines and myeloma cell lines. The recombinant protein gene will be operably linked to appropriate expression control sequences for each host. For E. coli this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences. In one particularly preferred embodiment the GM-CSF-G250 fusion gene is inserted into polyhedrin gene locus-based baculovirus transfer vector (e.g., pVL 1393, available from PharMingen) and expressed in insect cells (e.g. SF9 cells).

The plasmids of the invention can be transferred into the chosen host cell by well-known methods such as calcium chloride transformation for E. coli and calcium phosphate treatment or electroporation for mammalian cells. Cells transformed by the plasmids can be selected by resistance to antibiotics conferred by genes contained on the plasmids, such as the amp, gpt, neo, and hyg genes.

Once expressed, the recombinant fusion proteins can be purified according to standard procedures of the art, including ammonium sulfate precipitation, his tag capture, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification.*, Academic Press, Inc. N.Y. (1990)). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the G250, GM-CSF, or GM-CSF-G250 protein may possess a conformation substantially different than the native conformations of the polypeptide(s). In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.*, 268: 14065-14070; Kreitman and Pastan, (1993) *Bioconjug. Chem.*, 4: 581-585; and Buchner, et al., (1992) *Anal. Biochem.*, 205: 263-270). Debinski et al., for example, describe the denaturation and reduction of inclusion body proteins in guanidine-DTE. The protein is then refolded in a redox buffer containing oxidized glutathione and L-arginine.

One of skill would recognize that modifications can be made to the GM-CSF, G250, or GM-CSF-G250 proteins without diminishing their biological activity. Some modifications may be made to facilitate the cloning, expression, or incorporation of the constituent molecules into a fusion protein. Such modifications are well known to those of skill in the art and include, for example, a methionine added at the amino terminus to provide an initiation site, or additional amino acids placed on either terminus to create conveniently located restriction sites or termination codons. The recombinant expression of a GM-CSF-G250 fusion protein is illustrated in Example 1.

II. In Vivo Protein Vaccination.

Immunogenic compositions (e.g. vaccines) are preferably prepared from the G250-GM-CSF fusion proteins of this invention. The immunogenic compositions including vaccines may be prepared as injectables, as liquid solutions, suspensions or emulsions. The active immunogenic ingredient or ingredients may be mixed with pharmaceutically acceptable excipients which are compatible therewith. Such excipients are well known to those of skill in the art and include, but are not limited to water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof.

The immunogenic G250-GM-CSF compositions may be administered parenterally, by injection subcutaneous, intravenous, intradermal, intratumoral, or intramuscularly injection. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Such suppositories may be formed from mixtures containing the active immunogenic ingredient (s) in the range of about 0.5 to about 10%, preferably about 1 to 2%. Oral formulations may include normally employed carriers such pharmaceutical grades of saccharine, cellulose and magnesium carbonate. These compositions can take the form of solutions, suspensions, tablets, pills, capsules, sustained release formulations or powders and contain about 1 to 95% of the active ingredient(s), preferably about 20 to about 75%.

The immunogenic preparations and vaccines are administered in a manner compatible with the dosage formulation, and in such amount as will be therapeutically effective, immunogenic and protective. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms to milligrams of the active ingredient(s)

per vaccination. The antigenic preparations of this invention can be administered by either single or multiple dosages of an effective amount. Effective amounts of the compositions of the invention can vary from 0.01-1,000 µg/ml per dose, more preferably 0.1-500 µg/ml per dose, and most preferably 10-300 µg/ml per dose.

Suitable regimes for initial administration and booster doses are also variable, but may include an initial administration followed by subsequent booster administrations. The dosage may also depend or the route of administration and will vary according to the size of the host.

The concentration of the active ingredient (chimeric protein) in an immunogenic composition according to the invention is in general about 1 to 95%.

Immunogenicity can be significantly improved if the antigens are co-administered with adjuvants. While the GM-CSF component of the chimeric molecule can, itself act as an adjuvant, other adjuvants can be used as well. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and a HBsAg vaccine has been adjuvanted with alum A wide range of extrinsic adjuvants can provoke potent immune responses to antigens. These include saponins complexed to membrane protein antigens (immune stimulating complexes, pluronic polymers with mineral oil, killed mycobacteria in mineral oil, Freund's incomplete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are often emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

III. In Vivo DNA Vaccination.

In some preferred embodiments, nucleic acids encoding a G250-GM-CSF fusion protein are incorporated into DNA vaccines. The ability of directly injected DNA, that encodes an antigenic protein, to elicit a protective immune response has been demonstrated in numerous experimental systems (see, e.g., Conry et al. (1994) *Cancer Res.*, 54: 1164-1168; Cox et al. (1993) *Virol*, 67: 5664-5667; Davis et al. (1993) *Hum. Mole. Genet.*, 2: 1847-1851; Sedegah et al. (1994) *Proc. Natl. Acad. Sci., USA*, 91: 9866-9870; Montgomery et al. (1993) *DNA Cell Bio.*, 12: 777-783; Ulmer et al. (1993) *Science*, 259: 1745-1749; Wang et al. (1993) *Proc. Natl. Acad. Sci., USA*, 90: 4156-4160; Xiang et al. (1994) *Virology*, 199: 132-140, etc.).

Vaccination through directly injecting DNA, that encodes an antigenic protein, to elicit a protective immune response often produces both cell-mediated and humoral responses. Moreover, reproducible immune responses to DNA encoding various antigens have been reported in mice that last essentially for the lifetime of the animal (see, e.g., Yankauckas et al. (1993) *DNA Cell Biol.*, 12: 771-776).

As indicated above, DNA vaccines are known to those of skill in the art (see, also U.S. Pat. Nos. 5,589,466 and 5,593,971, PCT/US90/01515, PCT/US93/02338, PCT/US93/048131, PCT/US94/00899, and the priority applications cited therein. In addition to the delivery protocols described in those applications, alternative methods of delivering DNA are described in U.S. Pat. Nos. 4,945,050 and 5,036,006.

Using DNA vaccine technology, plasmid (or other vector) DNA that includes a sequence encoding a G250-GM-CSF fusion protein operably linked to regulatory elements required for gene expression is administered to individuals (e.g. human patients, non-human mammals, etc.). The cells of the individual take up the administered DNA and the coding sequence is expressed. The antigen so produced becomes a target against which an immune response is directed. In the present case, the immune response directed against the antigen component of the chimeric molecule provides the prophylactic or therapeutic benefit to the individual renal cell cancers.

The vaccines of this invention may be administered by a variety of techniques including several different devices for administering substances to tissue. The published literature includes several review articles that describe aspects of DNA vaccine technology and cite some of the many reports of results obtained using the technology (see, e.g., McDonnel and Askari (1996) *New Engl. J. Med.* 334(1): 42-45; Robinson (1995) *Can. Med. Assoc. J.* 152(10): 1629-1632; Fynan et al. (1995) *Int. J. Immunopharmac.* 17(2): 79-83; Pardoll and Beckerleg (1995) *Immunity* 3: 165-169; and Spooner et al. (1995) *Gene Therapy* 2: 173-180.

According to the present invention, the G250-GM-CSF coding sequence is inserted into a plasmid (or other vector) which is then used in a vaccine composition. In preferred embodiments, the G250-GM-CSF coding sequence is operably linked to regulatory elements required for expression of the construct in eukaryotic cells. Regulatory elements for DNA expression include, but are not limited to a promoter and a polyadenylation signal. In addition, other elements, such as a Kozak region, may also be included in the genetic construct. Initiation and termination signals are regulatory elements which are often, but not necessarily, considered part of the coding sequence. In preferred embodiments, the coding sequences of genetic constructs of this invention include functional initiation and termination signals.

Examples of promoters useful to practice the present invention, especially in the production of a genetic vaccine for humans, include but are not limited to, promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal which is in pCEP4 plasmid (Invitrogen, San Diego, Calif.), referred to as the SV40 polyadenylation signal, may be used.

In addition to the regulatory elements required for DNA expression, other elements may also be included in the DNA molecule. Such additional elements include enhancers. The enhancer may be selected from the group including but not limited to, human Actin, human Myosin, human Hemoglobin, human muscle creatine and viral enhancers such as those from CMV, RSV and EBV.

The present invention relates to methods of introducing genetic material into the cells of an individual in order to induce immune responses against renal cell cancers. The methods comprise the steps of administering to the tissue of said individual, DNA that includes a coding sequence for a G250-GM-CSF fusion protein operably linked to regulatory elements required for expression. The DNA can be administered in the presence of adjuvants or other substances that have the capability of promoting DNA uptake or recruiting immune system cells to the site of the inoculation. It should be understood that, in preferred embodiments, the DNA transcription unit itself is expressed in the host cell by transcription factors provided by the host cell, or provided by a DNA transcriptional unit. A DNA transcription unit can comprise nucleic acids that encode proteins that serve to stimulate the immune response such as a cytokine, proteins that serve as an adjuvant and proteins that act as a receptor.

Vectors containing the nucleic acid-based vaccine of the invention can be introduced into the desired host by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al (1992) *J. Biol. Chem.* 267: 963-967; Wu and Wu (1988) *J. Biol. Chem.* 263: 14621-14624). The subject can be inoculated intramuscularly, intranasally, intraperatoneally, subcutaneously, intradermally, topically, or by a gene gun.

The subject can also be inoculated by a mucosal route. The DNA transcription unit can be administered to a mucosal surface by a variety of methods, including lavage, DNA-containing nose-drops, inhalants, suppositories or by microsphere encapsulated DNA. For example, the DNA transcription unit can be administered to a respiratory mucosal surface, such as the trachea or into any surface including the tongue or mucous membrane.

The DNA transcription units are preferably administered in a medium, i.e., an adjuvant, that acts to promote DNA uptake and expression. Preferably, a pharmaceutically acceptable, inert medium is suitable as an adjuvant for introducing the DNA transcription unit into the subject. One example of a suitable adjuvant is alum (alumina gel), though even a saline solution is acceptable. Other possible adjuvants include organic molecules such as squalines, iscoms, organic oils and fats.

An immuno-effector can be co-expressed with the G250-GM-CSF nucleic acid of this present invention and thereby enhance the immune response to the antigen. A nucleic acid encoding the immuno-effector may be administered in a separate DNA transcription unit, operatively linked to a suitable DNA promoter, or alternatively the immuno-effector may be included in a DNA transcription unit comprising a nucleic acid that encodes the G250-GM-CSF construct that are operatively linked to one or more DNA promoters. Other embodiments contain two or more such immuno-effectors operatively linked to one or more promoters. The nucleic acid can consist of one contiguous polymer, encoding both the chimeric protein and the immuno-effector or it can consist of independent nucleic acid segments that individually encode the chimeric molecule and the immuno-effector respectively. In the latter case, the nucleic acid may be inserted into one vector or the independent nucleic acid segments can be placed into separate vectors. The nucleic acid encoding the inmuno-effector and the chimeric molecule may be either operatively linked to the same DNA promoter or operatively linked to separate DNA promoters. Adding such an immuno-effector is known in the art. Alternatively, soluble immuno-effector proteins (cytokines, monokines, interferons, etc.) can be directly administered into the subject in conjunction with the G250-GM-CSF DNA.

Examples of immuno-effectors include, but are not limited to, interferon-α, interferon-γ, interferon-β, interferon-θ, interferon-τ, tumor necrosis factor-α, tumor necrosis factor-β, interleukin-2, interleukin-6, interleukin-7, interleukin-12, interleukin-15, B7-1 T cell co-stimulatory molecule, B7-2 T cell co-stimulatory molecule, immune cell adhesion molecule (ICAM)-1, T cell co-stimulatory molecule, granulocyte colony stimulating factor, granulocyte-macrophage colony stimulating factor, and combinations thereof.

When taken up by a cell, the genetic construct(s) may remain present in the cell as a functioning extrachromosomal molecule and/or integrate into the cell's chromosomal DNA. DNA may be introduced into cells where it remains as separate genetic material, e.g., in the form of a plasmid or plasmids. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal.

Genetic constructs can be provided with a mammalian origin of replication in order to maintain the construct extrachromosomally and produce multiple copies of the construct in the cell. Thus, for example, plasmids pCEP4 and pREP4 from Invitrogen (San Diego, Calif.) contain the Epstein Barr virus origin of replication and nuclear antigen EBNA-1 coding region which produces high copy episomal replication without integration.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the G250-GM-CSF nucleic acid construct.

In order to maximize protein production, regulatory sequences may be selected which are well suited for gene expression in the cells into which the construct is administered. Moreover, codons may be selected which are most efficiently transcribed in the cell. One having ordinary skill in the art can produce DNA constructs which are functional in the cells.

The concentration of the dosage is preferably sufficient to provide an effective immune response. The dosage of the recombinant vectors administered will depend upon the properties of the formulation employed, e.g., its in vivo plasma half-life, the concentration of the recombinant vectors in the formulation, the administration route, the site and rate of dosage, the clinical tolerance of the subject, and the like, as is well within the skill of one skilled in the art. Different dosages may be utilized in a series of inoculations; the practitioner may administer an initial inoculation and then boost with relatively smaller doses of the recombinant vectors or other boosters.

The preferred dose range is between about 30 μg to about 1 mg DNA, and more preferably between about 50 μg to 500 μg. Lower doses may be used as plasmid expression and inoculation are optimized. Dosages may differ for adults in contrast to adolescents or children. The inoculation is preferably followed by boosters.

IV. Adoptive Immunotherapy.

Adoptive immunotherapy refers to a therapeutic approach for treating cancer or infectious diseases in which immune cells are administered to a host with the aim that the cells mediate either directly or indirectly specific immunity to (i.e., mount an immune response directed against) tumor cells. In preferred embodiments, the immune response results in inhibition of tumor and/or metastatic cell growth and/or proliferation and most preferably results in neoplastic cell death and/or resorption. The immune cells can be derived from a different organism/host (exogenous immune cells) or can be cells obtained from the subject organism (autologous immune cells).

The immune cells are typically activated in vitro by a particular antigen (in this case G250), optionally expanded, and then re-infused back into the source organism (e.g., patient). Methods of performing adoptive immunotherapy are well known to those of skill in the art (see, e.g., U.S. Pat. Nos. 5,081,029, 5,985,270, 5,830,464, 5,776,451, 5,229,115, 690,915, and the like).

In preferred embodiments, this invention contemplates numerous modalities of adoptive immunotherapy, e.g. as described above. In one embodiment, dendritic cells (e.g. isolated from the patient or autologous dendritic cells) are pulsed with G250 or the G250-GM-CSF chimeric molecule and then injected back into the subject where they present and activate immune cells in vivo. In addition, or alternatively, the dentritic cells can be transfected with nucleic acids encoding the G250-GM-CSF fusion protein and then re-introduced into a patient.

In another embodiment, modified macrophage or dendritic cell (antigen presenting cells) are pulsed with G250-GM-CSF fusion proteins or transfected with nucleic acids encoding a G250-GM-CSF fusion protein, and then used to stimulate peripheral blood lymphocytes or TIL in culture and activate G250-targeted CTLs that are then infused into the patient.

Similarly, fibroblasts, and other APCs, or tumor cells (e.g. RCCs) are transfected with a nucleic acid expressing a G250-GM-CSF and used to activate tumor cells or PBLs ex vivo to produce G250 directed CTLs that can then be infused into a patient.

Similarly various "transfection agents" including, but not limited to gene therapy vectors (e.g. adenovirus, gutless-adenovirus, retrovirus, lantivirus, adeno-associated virus, vaccinia virus etc), cationic lipids, liposomes, dendrimers, and the like, containing or complexed with a nucleic acid encoding a G250-GM-CSF fusion protein are administered to PBLs or to tumor cells (e.g. RCCs) ex vivo to produce G250 directed CTLs.

In one particularly preferred embodiments, tumor cells (e.g. RCC cells) transfected to express a G250-GM-CSF protein are used to provide an off-the-shelf vaccine effective against tumors expressing a G250 antigen or an antigen that is cross-reactive with G250.

Using the teachings provided herein, other therapeutic modalities utilizing G250-GM-CSF polypeptides or G250-GM-CSF nucleic acids can be readily developed.

As indicated above, in one embodiment the immune cells are derived from peripheral blood lymphocytes or TILs (e.g. derived from tumors/tumor suspension). Lymphocytes used for in vitro activation include, but are not limited to T lymphocytes, various antigen presenting cells (e.g. monocytes, dendritic cells, B cells, etc.) and the like. Activation can involve contacting an antigen presenting cell with the chimeric molecule(s) of this invention which then present the G250 antigen (or fragment thereof), e.g., on HLA class I molecules and/or on HLA class II molecules, and/or can involve contacting a cell (e.g. T-lymphocyte) directly with the chimeric molecule. The antigen-presenting cells (APCs), including but not limited to macrophages, dendritic cells and B-cells, are preferably obtained by production in vitro from stem and progenitor cells from human peripheral blood or bone marrow as described by Inaba et al., (1992) *J. Exp. Med.* 176: 1693-1702.

Activation of immune cells can take a number of forms. These include, but are not limited to the direct addition of the chimeric molecule to peripheral blood lymphocytes (PBLs) or tumor infiltrating lymphocytes (TILs) in culture, loading of antigen presenting cells (e.g. monocytes, dendritic cells, etc.) with the chimeric molecule in culture, transfection of antigen presenting cells, or PBLs, with a nucleic acid encoding the GM-CSF-G250 chimeric fusion protein, and the like.

APC can be obtained by any of various methods known in the art. In a preferred aspect human macrophages and/or dendritic cells are used, obtained from human blood donors. By way of example but not limitation, PBLs (e.g. T-cells) can be obtained as follows:

Approximately 200 ml of heparinized venous blood is drawn by venipuncture and PBL are isolated by Ficoll-hypaque gradient centrifugation, yielding approximately 1 to $5 \times 10^8$ PBL, depending upon the lymphocyte count of the donor(s). The PBL are washed in phosphate-buffered saline and are suspended at approximately $2 \times 10^5$/ml in RPMI 1640 medium containing 10% pooled heat-inactivated normal human serum; this medium will be referred to as "complete medium."

Similarly, other cells (e.g. mononuclear cells) are isolated from peripheral blood of a patient (preferably the patient to be treated), by Ficoll-Hypaque gradient centrifugation and are seeded on tissue culture dishes which are pre-coated with the patient's own serum or with other AB+ human serum. The cells are incubated at 37° C. for 1 hr, then non-adherent cells are removed by pipetting. To the adherent cells left in the dish, is added cold (4° C.) 1 mM EDTA in phosphate-buffered saline and the dishes are left at room temperature for 15 minutes. The cells are harvested, washed with RPMI buffer and suspended in RPMI buffer. Increased numbers of macrophages may be obtained by incubating at 37° C. with macrophage-colony stimulating factor (M-CSF); increased numbers of dendritic cells may be obtained by incubating with granulocyte-macrophage-colony stimulating factor (GM-CSF) as described in detail by Inaba et al. (1992) *J. Exp. Med.* 176:1693-1702, and more preferably by incubating with the G250-GM-CSF chimeric molecules of this invention and, optionally IL-4).

The cells (e.g. APCs) are sensitized by contacting/incubating them with the chimeric molecule. In some embodiments, sensitization may be increased by contacting the APCs with heat shock protein(s) (hsp) noncovalently bound to the chimeric molecule. It has been demonstrated that hsps noncovalently bound to antigenic molecules can increase APC sensitization in adoptive immunotherapeutic applications (see, e.g., U.S. Pat. No. 5,885,270).

In one preferred embodiment, e.g. as described in the examples herein, G250-GM-CSF fusion protein (with optional IL-4) is added into the patients PBMC ex vivo and then cultured at 37° C. for 7 days. The culture is re-stimulated weekly with IL-2 and fusion protein, e.g. for 4 to 5 cycles until the culture shows anti-tumor activity against autologous kidney tumor cells displaying G250. The CTLs are then reinfused back into the patient.

For re-infusion, the cells are washed three times and resuspended in a physiological medium preferably sterile, at a convenient concentration (e.g., $1 \times 10^7$/ml) for injection in a patient. The cell suspension is then filtered, e.g., through sterile 110 mesh and put into Fenwall transfer packs. Samples of the cells are tested for the presence of microorganisms including fungi, aerobic and anaerobic bacteria, and mycoplasma. A sample of the cells is optionally retained for immunological testing in order to demonstrate induction of specific immunity.

In a preferred embodiment, before use in immunotherapy, the stimulated lymphocytes are tested for cell-mediated immune reactivity against tumor cells bearing the G250 antigen. The PBL/TIL, following stimulation with the chimeric molecules of this invention can be examined with regard to cell surface expression of T and B cell markers by immunofluorescent analysis using fluorescein-conjugated monoclonal antibodies to T and B cell antigens. Expression of known T cell markers, such as the CD4 and CD8 antigens, confirms the identity of the activated lymphocytes as T cells.

The activated cells (e.g. activated T cells) are then, optionally, tested for reactivity against G250. This could be accomplished by any of several techniques known in the art for assaying specific cell-mediated immunity. For example, a cytotoxicity assay, which measures the ability of the stimulated T cells to kill tumor cells bearing the G250 antigen in vitro, may be accomplished by incubating the lymphocytes with G250-bearing tumor cells containing a marker (e.g. $^{51}$Cr-labelled cells) and measuring $^{51}$Cr release upon lysis. Such assays have been described (see, e.g., Zarling et al. (1986) *J. Immunol.* 136: 4669). The activated PBL could also be tested for T helper cell activity by measuring their ability to proliferate, as shown by $^3$H-thymidine incorporation, following stimulation, and/or by measuring their ability to produce lymphokines such as IL-2 or interferon upon stimulation, in the absence of exogenous IL-2. Other assays of specific cell-mediated immunity known in the art, such as leukocyte-adherence inhibition assays (Thomson, D. M. P. (ed.), 1982, Assessment of Immune Status by the Leukocyte Adherence Inhibition Test, Academic Press, New York), may also be used.

Inoculation of the activated cells is preferably through systemic administration. The cells can be administered intravenously through a central venous catheter or into a large peripheral vein. Other methods of administration (for example, direct infusion into an artery) are within the scope of the invention. Approximately $1 \times 10^8$ cells are infused initially and the remainder are infused over the following several hours. In some regimens, patients may optionally receive in addition a suitable dosage of a biological response modifier including but not limited to the cytokines IFN-α, IFN-γ, IL-2, TNF or other cytokine growth factor, antisense TGFβ, antisense IL-10, and the like. Thus, in some patients, recombinant human IL-2 may be used and will be infused intravenously every 8 hours beginning at the time of T cell infusion. Injections of IL-2 will preferably be at doses of 10,000 to 100,000 units/kg bodyweight, as previously used in cancer patients (Rosenberg et al. (1985) *N. Engl. J. Med.* 313: 1485). The IL-2 infusion may be continued for several days after infusion of the activated T cells if tolerated by the patient.

Treatment by inoculation of, e.g., activated T cells can be used alone or in conjunction with other therapeutic regimens including but not limited to administration of IL-2 (as described supra), other chemotherapeutics (e.g. doxirubicin, vinblastine, vincristine, etc.), radiotherapy, surgery, and the like.

As indicated above, the cells may, optionally, be expanded in culture. This expansion can be accomplished by repeated stimulation of the T cells with the G250-GM-CSF construct of this invention with or without IL-2 or by growth in medium containing IL-2 alone. Other methods of T cell cultivation (for example with other lymphokines, growth factors, or other bioactive molecules) are also within the scope of the invention. For example, antibodies or their derivative molecules which recognize the Tp67 or Tp44 antigens on T cells have been shown to augment proliferation of activated T cells (Ledbetter et al. (1985) *J. Immunol.* 135: 2331), and may be used during in vitro activation to increase proliferation. Interferon has been found to augment the generation of cytotoxic T cells (Zarling et al. (1978) *Immunol.* 121: 2002), and may be used during in vitro activation to augment the generation of cytotoxic T cells against G250 bearing cancer cells.

The description provided above details various methods for isolation, activation, and expansion of PBL. However the present invention provides for the use G250-GM-CSF constructs in various forms, and modifications and adaptations to the method to accommodate these variations. Thus modifications of various adoptive immunotherapeutic approaches utilizing the G250-GM-CSF constructs are within the scope of the invention.

V. Gene Transfer for Systemic Therapy or for Adoptive Immunotherapy.

In addition to use of the chimeric GM-CSF-G250 chimeric protein for activation in adoptive immunotherapy, cells, (e.g., APCs, PBLs, fibroblasts, TILs, or RCC tumor cells) can be transfected with a vector expressing the chimeric molecule and used for adoptive immunotherapy and/or vaccine therapy.

In one preferred embodiment, the nucleic acid(s) encoding the GM-CSF-G250 chimeric fusion proteins are cloned into gene therapy vectors that are competent to transfect cells (such as human or other mammalian cells) in vitro and/or in vivo.

Several approaches for introducing nucleic acids into cells in vivo, ex vivo and in vitro have been used. These include lipid or liposome based gene delivery (WO 96/18372; WO 93/24640; Mannino and Gould-Fogerite (1988) *BioTechniques* 6(7): 682-691; Rose U.S. Pat. No. 5,279,833; WO 91/06309; and Feigner et al. (1987) *Proc. Natl. Acad. Sci. USA* 84: 7413-7414) and replication-defective retroviral vectors harboring a therapeutic polynucleotide sequence as part of the retroviral genome (see, e.g., Miller et al. (1990) *Mol. Cell. Biol.* 10: 4239 (1990); Kolberg (1992) *J. NIH Res.* 4: 43, and Cornetta et al. (1991) *Hum. Gene Ther.* 2: 215).

For a review of gene therapy procedures, see, e.g., Anderson, *Science* (1992) 256: 808-813; Nabel and Feigner (1993) *TIBTECH* 11: 211-217; Mitani and Caskey (1993) *TIBTECH* 11: 162-166; Mulligan (1993) *Science*, 926-932; Dillon (1993) *TIBTECH* 11: 167-175; Miller (1992) *Nature* 357: 455-460; Van Brunt (1988) *Biotechnology* 6(10): 1149-1154; Vigne (1995) Restorative Neurology and Neuroscience 8: 35-36; Kremer and Perricaudet (1995) *British Medical Bulletin* 51(1) 31-44; Haddada et al. (1995) in *Current Topics in Microbiology and Immunology*, Doerfler and Böhm (eds) Springer-Verlag, Heidelberg Germany; and Yu et al., (1994) *Gene Therapy*, 1: 13-26.

Widely used retroviral vectors include those based upon murine leukemia virus (MuLV), gibbon ape leukemia virus (GaLV), Simian Immunodeficiency virus (SN), human immunodeficiency virus (HIV), alphavirus, and combinations thereof (see, e.g., Buchscher et al. (1992) *J. Virol.* 66(5) 2731-2739; Johann et al. (1992) *J. Virol.* 66 (5): 1635-1640 (1992); Sommerfelt et al., (1990) *Virol.* 176: 58-59; Wilson et al. (1989) *J. Virol.* 63: 2374-2378; Miller et al., *J. Virol.* 65: 2220-2224 (1991); Wong-Staal et al., PCT/US94/05700, and Rosenburg and Fauci (1993) in Fundamental Immunology, Third Edition Paul (ed) Raven Press, Ltd., New York and the references therein, and Yu et al. (1994) *Gene Therapy*, supra; U.S. Pat. No. 6,008,535, and the like).

The vectors are optionally pseudotyped to extend the host range of the vector to cells which are not infected by the retrovirus corresponding to the vector. For example, the vesicular stomatitis virus envelope glycoprotein (VSV-G) has been used to construct VSV-G-pseudotyped HIV vectors which can infect hematopoietic stem cells (Naldini et al. (1996) *Science* 272: 263, and Akkina et al. (1996) *J Virol* 70: 2581).

Adeno-associated virus (AAV)-based vectors are also used to transduce cells with target nucleic acids, e.g., in the in vitro production of nucleic acids and peptides, and in in vivo and ex vivo gene therapy procedures. See, West et al. (1987) *Virology* 160: 38-47; Carter et al. (1989) U.S. Pat. No. 4,797,368; Carter et al. WO 93/24641 (1993); Kotin (1994) *Human Gene Therapy* 5: 793-801; Muzyczka (1994) *J. Clin. Invst.* 94: 1351 for an overview of AAV vectors. Construction of recombinant AAV vectors are described in a number of publications, including Lebkowski, U.S. Pat. No. 5,173,414; Tratschin et al. (1985) *Mol. Cell. Biol.* 5(11): 3251-3260; Tratschin, et al. (1984) *Mol. Cell. Biol.*, 4: 2072-2081; Hermonat and Muzyczka (1984) *Proc. Natl. Acad. Sci. USA*, 81: 6466-6470; McLaughlin et al. (1988) and Samulski et al. (1989) *J. Virol.*, 63: 03822-3828. Cell lines that can be transformed by rAAV include those described in Lebkowski et al. (1988) *Mol. Cell. Biol.*, 8: 3988-3996. Other suitable viral vectors include herpes virus, lentivirus, and vaccinia virus.

In addition to viral vectors, a number of non-viral transfection methods are available. Such methods include, but are not limited to electroporation methods, calcium phosphate transfection, liposomes, cationic lipid complexes, water-oil emulsions, polethylene imines, and dendrimers.

Liposomes were first described in 1965 as a model of cellular membranes and quickly were applied to the delivery of substances to cells. Liposomes entrap DNA by one of two mechanisms which has resulted in their classification as either cationic liposomes or pH-sensitive liposomes. Cationic liposomes are positively charged liposomes which interact with the negatively charged DNA molecules to form a stable complex. Cationic liposomes typically consist of a positively charged lipid and a co-lipid. Commonly used co-lipids include dioleoyl phosphatidylethanolamine (DOPE) or dioleoyl phosphatidylcholine (DOPC). Co-lipids, also called helper lipids, are in most cases required for stabilization of liposome complex. A variety of positively charged lipid formulations are commercially available and many other are under development. Two of the most frequently cited cationic lipids are lipofectamine and lipofectin. Lipofectin is a commercially available cationic lipid first reported by Phil Feigner in 1987 to deliver genes to cells in culture. Lipofectin is a mixture of N-[1-(2, 3-dioleyloyx) propyl]-N—N—N-trimethyl ammonia chloride (DOTMA) and DOPE.

DNA and lipofectin or lipofectamine interact spontaneously to form complexes that have a 100% loading efficiency. In other words, essentially all of the DNA is complexed with the lipid, provided enough lipid is available. It is assumed that the negative charge of the DNA molecule interacts with the positively charged groups of the DOTMA. The lipid:DNA ratio and overall lipid concentrations used in forming these complexes are extremely important for efficient gene transfer and vary with application. Lipofectin has been used to deliver linear DNA, plasmid DNA, and RNA to a variety of cells in culture. Shortly after its introduction, it was shown that lipofectin could be used to deliver genes in vivo. Following intravenous administration of lipofectin-DNA complexes, both the lung and liver showed marked affinity for uptake of these complexes and transgene expression. Injection of these complexes into other tissues has had varying results and, for the most part, are much less efficient than lipofectin-mediated gene transfer into either the lung or the liver.

PH-sensitive, or negatively-charged liposomes, entrap DNA rather than complex with it. Since both the DNA and the lipid are similarly charged, repulsion rather than complex formation occurs. Yet, some DNA does manage to get entrapped within the aqueous interior of these liposomes. In some cases, these liposomes are destabilized by low pH and hence the term pH-sensitive. To date, cationic liposomes have been much more efficient at gene delivery both in vivo and in vitro than pH-sensitive liposomes. pH-sensitive liposomes have the potential to be much more efficient at in vivo DNA delivery than their cationic counterparts and should be able to do so with reduced toxicity and interference from serum protein.

In another approach dendrimers complexed to the DNA have been used to transfect cells. Such dendrimers include, but are not limited to, "starburst" dendrimers and various dendrimer polycations.

Dendrimer polycations are three dimensional, highly ordered oligomeric and/or polymeric compounds typically formed on a core molecule or designated initiator by reiterative reaction sequences adding the oligomers and/or polymers and providing an outer surface that is positively changed. These dendrimers may be prepared as disclosed in PCT/US83/02052, and U.S. Pat. Nos. 4,507,466, 4,558,120, 4,568,737, 4,587,329, 4,631,337, 4,694,064, 4,713,975, 4,737,550, 4,871,779, 4,857,599.

Typically, the dendrimer polycations comprise a core molecule upon which polymers are added. The polymers may be oligomers or polymers which comprise terminal groups capable of acquiring a positive charge. Suitable core molecules comprise at least two reactive residues which can be utilized for the binding of the core molecule to the oligomers and/or polymers. Examples of the reactive residues are hydroxyl, ester, amino, imino, imido, halide, carboxyl, carboxyhalide maleimide, dithiopyridyl, and sulfhydryl, among others. Preferred core molecules are ammonia, tris-(2-aminoethyl)amine, lysine, ornithine, pentaerythritol and ethylenediamine, among others. Combinations of these residues are also suitable as are other reactive residues.

Oligomers and polymers suitable for the preparation of the dendrimer polycations of the invention are pharmaceutically-acceptable oligomers and/or polymers that are well accepted in the body. Examples of these are polyamidoamines derived from the reaction of an alkyl ester of an α, β-ethylenically unsaturated carboxylic acid or an α, β-ethylenically unsaturated amide and an alkylene polyamine or a polyalkylene polyamine, among others. Preferred are methyl acrylate and ethylenediamine. The polymer is preferably covalently bound to the core molecule.

The terminal groups that may be attached to the oligomers and/or polymers should be capable of acquiring a positive charge. Examples of these are azoles and primary, secondary, tertiary and quaternary aliphatic and aromatic amines and azoles, which may be substituted with S or O, guanidinium, and combinations thereof. The terminal cationic groups are preferably attached in a covalent manner to the oligomers and/or polymers. Preferred terminal cationic groups are amines and guanidinium. However, others may also be utilized. The terminal cationic groups may be present in a proportion of about 10 to 100% of all terminal groups of the oligomer and/or polymer, and more preferably about 50 to 100%.

The dendrimer polycation may also comprise 0 to about 90% terminal reactive residues other than the cationic groups. Suitable terminal reactive residues other than the terminal cationic groups are hydroxyl, cyan, carboxyl, sulfhydryl, amide and thioether, among others, and combinations thereof. However others may also be utilized.

The dendrimer polycation is generally and preferably non-covalently associated with the polynucleotide. This permits an easy disassociation or disassembling of the composition once it is delivered into the cell. Typical dendrimer polycation suitable for use herein have a molecular weight ranging from about 2,000 to 1,000,000 Da, and more preferably about 5,000 to 500,000 Da. However, other molecule weights are also suitable. Preferred dendrimer polycations have a hydrodynamic radius of about 11 to 60 Å., and more preferably about 15 to 55 Å. Other sizes, however, are also suitable. Methods for the preparation and use of dendrimers in gene therapy are well known to those of skill in the art and describe in detail, for example, in U.S. Pat. No. 5,661,025

Where appropriate, two or more types of vectors can be used together. For example, a plasmid vector may be used in conjunction with liposomes. In the case of non-viral vectors, nucleic acid may be incorporated into the non-viral vectors by any suitable means known in the art. For plasmids, this typically involves ligating the construct into a suitable restriction site. For vectors such as liposomes, water-oil emulsions, polyethylene amines and dendrimers, the vector and construct may be associated by mixing under suitable conditions known in the art.

VI. Administration of GM-CSF-G250 with Other Agents.

In various embodiments, the GM-CSF-G250 fusion proteins, or nucleic acids encoding the GM-CSF-G250 fusion proteins can be administered in conjunction with other agents. Such agents include, but are not limited to various chemotherapeutic agents (e.g. doxirubicin and derivatives, taxol and derivatives, vinblastine, vincristine, camptothecin derivatives, and the like, various cytokines (e.g. IL-2, IL-7, IL-12, IFN, etc.), various cytotoxins (e.g. *Pseudomonas* exotoxin and derivatives, diphtheria toxin and derivatives, ricin and derivatives, abrin and derivatives, thymidine kinase and derivatives), antisense molecules (e.g. antisense IL-10, TGF-(β, etc.), antibodies against various growth factors/receptors (e.g. anti-VEGF, anti-EGFR, anti-IL-8, anti-FGF etc.), and the like. The methods of this invention can also be used as a adjunct to surgery, and/or radiotherapy.

VII. Kits.

Kits of the invention are provided that include materials/reagents useful for vaccination using a polypeptide antigen (GM-CSF-G250 polypeptide) and/or DNA vaccination, and/or adoptive immunotherapy. Kits optimized for GM-CSF-G250 polypeptide vaccination preferably comprise a container containing a GM-CSF-G250 chimeric molecule. The molecule can be provided in solution, in suspension, or as a (e.g. lyophilized) powder. The GM-CSF-G250 may be packaged with appropriate pharmaceutically acceptable excipient and/or adjuvant, e.g. in a unit dosage form.

Similarly, kits optimized for DNA vaccination of a construct encoding a GM-CSF-G250 polypeptide preferably comprise a container containing a GM-CSF-G250 nucleic acid (e.g. a DNA). As with the polypeptide, the nucleic acid can be provided in solution, in suspension, or as a (e.g. lyophilized) powder. The GM-CSF-G250 nucleic may be packaged with appropriate pharmaceutically acceptable excipient and/or facilitating agent(s), e.g. in a unit dosage form. The kit can further include reagents and/or devices to facilitate delivery of the nucleic acid to the subject (e.g. human or non-human mammal).

Kits optimized for adoptive immunotherapy typically include a container containing a chimeric GM-CSF-G250 polypeptide as described above. The kits may optionally include a nucleic acid (e.g. a vector) encoding a GM-CSF-G250 fusion protein for ex vivo transfection of cells. Such kits may also, optionally, include various cell lines (e.g. RCC) and/or reagents (e.g. 1L-2) to facilitate expansion of activated cells.

The kits can, optionally, include additional reagents (e.g. buffers, drugs, cytokines, cells/cell lines, cell culture media, etc.) and/or devices (e.g. syringes, biolistic devices, etc.) for the practice of the methods of this invention.

In addition, the kits may include instructional materials containing directions (i.e., protocols) for the practice of the methods of this invention. Thus typical instructional materials will teach the use of GM-CSF-G250 chimeric molecules (or the nucleic acid encoding such) as vaccines, DNA vaccines, or adoptive immunotherapeutic agents in the treatment of renal cell cancers. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Cloning and Expression of GM-CSF and G250 Fusion Protein

This example describes the cloning, expression and purification of a GM-CSF-G250 fusion protein.
Cloning of Human GM-CSF-G250 Fusion Gene A full-length human GM-CSF cDNA (0.8 kb) was cleaved from plasmid p91023(B) vector (Wong et al. (1985) Science 228: 810-815) with Eco RI restriction endonuclease. Eco RI (5') and Not I sites (3') were inserted into the GM-CSF cDNA by PCR (0.4 kb) using a first primer: gcggg aattc(atg)tggctgcagagc (5' GM-CSF Eco RI underlined, SEQ ID NO:5) and a second primer:

```
gagggaggcggccgc(ctc)ctggactggctc (3' GM-CSF Not I
underlined, to remove stop codon, SEQ ID NO: 6).
```

NotI (5') and His-Stop-Gbl II (3') sites were introduced into full length G250 cDNA (1.6 kb) by PCR using the following primers: 5' G250 (NotI): gagggagcggcc(gct)cccct-gtgcccc (remove start codon, SEQ ID NO:7), 3' G250-His-stop codon-Bgl II:

```
(1)
gcagaggtagagatct(cta)atggtgatggtgatggtgggctcca
gtctcggctacctc (SEQ ID NO: 8; brackets = stop
last, second underline = 8 His (SEQ ID NO: 27)), (2)
ggagagatct(cta)atgatgatgatgatgatgatgatgggctcca
gtctcggctacctct (SEQ ID NO: 9, brackets -stop
last, second underline = 8 His (SEQ ID NO: 27)).
```

Fragments were ligated producing M-CSF-NotI-G250-His-stop-Bgl II as follows:

5' (gag)ggcggcc(gct)cccctgtgcccc(rest of Gm-CSF-G250) (SEQ ID NO:10; where (gag) is the last of GM-CSF, and (gct) is the first of G250.

The 250 fusion gene was inserted into the polyhedrin gene locus-base baculovirus transfer vector pVL 1393 (PharMingen). In particular, the plasmid pVL 1393 was cut with Eco RI and Bgl II restriction endonucleases and the Eco RI-GM-CSF-G250-his-stop-Bgl II construct was inserted into the cut vector.

Insect cells (sf8 cells) were transfected using the BaculoGold transfection kit (Pharmingen). This involved co-transfection of linearized BaculoGold virus DNA and recombinant plasmid DNA containing GM-CSF-G250 fusion gene into insect cells (sf8 cells). The recombinant baculoviruses were amplified and the plaques were assayed to titer the virus.

The G250-GM-CSF protein was purified according to protocols provided in the Pharmigen Instruction Manual, 4th Edition, July 1997, page 41. Briefly beads were prepared by resuspending the Ni-NTA agarose beads. Two ml of beads were poured into 10 ml chromatography column (binding approximately 7.5-15 mg of 6×His fusion protein). The beads were allowed to settle in the column and the ethanol preservative was drained. The beads were then washed with 6×His wash buffer (Cat #21472A, Pharmigen) with 7.5 ml of 6×His wash buffer twice.

A cell lysate preparation was prepared by resuspending a cell pellet in ice-cold insect cell lysis buffer (Cat #21425A, Pharmigen) containing reconstituted protease inhibitor cocktail (Cat#21426Z, Pharmigen). The cells were lysed on ice for 45 minutes using 1 ml of lysis buffer per $2 \times 10^7$ cells).

The lysate was transferred into a clean centrifuge tube and centrifuged at 10,000 rpm for 30 minutes or filtered through a 0.22 μm filter. The supernatant was saved for the column and the pellet was discarded. 150 μl lysate was saved for an SDS-PAGE gel or Western blot and protein concentration determination.

Lysate was added to equilibrated Ni-NTA agarose beads for affinity purification on a column. The supernatant was loaded slowly or the beads were bound in a 15 ml conical tube with the lysate for 1 hour at 4° C. The flow-through fraction was saved.

The column was washed with 10-15 ml of 6×His wash buffer (Cat #21472A, Pharmigen) and the column was allowed to drain without drying. The wash step was repeated until the wash $A_{280}$ was less than 0.01 (approximately 4 washes).

The fusion protein was then eluted with imidazole. Briefly 4.5 ml of the 6×His elution buffer (Cat #21476A, Pharmigen) including imidazole was added as follows:
  i. 0.1 M imidazole with 6×His elution buffer;
  ii 0.2 M imidazole with 6×His elution buffer;
  iii 0.3 M imidazole with 6×His elution buffer;
  iv 0.4 M imidazole with 6×His elution buffer;
  v 0.5 M imidazole with 6×His elution buffer;

The elution speed was maintained at a rate less than or equal to 1 ml per minute. The eluted fractions were collected (200 μL).

After analysis with SDS-PAGE gel and Western Blot, the clean and correct fractions were picked and pooled, dialyzed against PBS and the Ni-NTA purification repeated again.

Once more after analysis with SDS-PAGE gel and Western Blot, the clean and correct fractions were picked and pooled, dialyzed against PBS. Further purification was performed on a Q-sepharose column. 1.0 ml of the column was equilibrated with 50 mM NaCl Buffer X (20 mM Hepes, 1 mM EDTA, 20% Glycerol, and 0.5 mM PMSF). The protein sample was loaded onto the column and the flow-through fraction was collected.

Further purification was performed on a SP-sepharose column. 1.0 ml of SP-sepharose column was loaded with 50 mM NaCl Buffer X (20 mM Hepes, 1 mM EDTA, 20% Glycerol, and 0.5 mM PMSF). The protein sample was loaded onto the column and the flow-through fraction was collected and saved. The column was eluted with the gradient salt buffer (50 mM NaCl Buffer X–1000 mM fraction are 5.0 ml and 0.1 ml, respectively). Elution was with 1000 mM NaCl buffer X.

The correct fractions were pooled and dialyzed against PBS.

Figure 2:
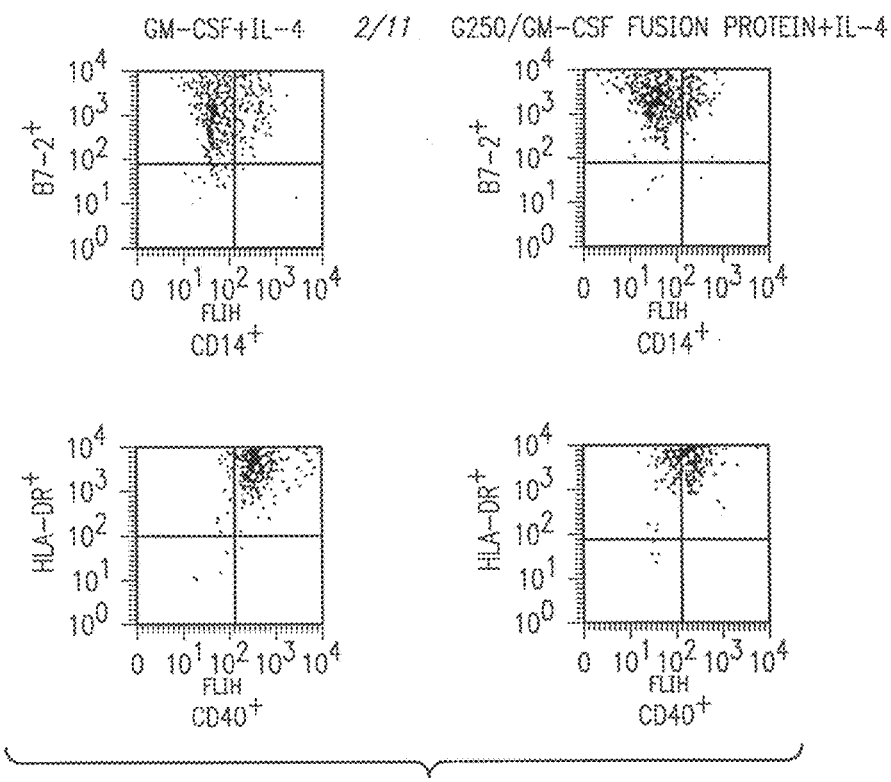
FIG. 2 illustrates FACS analysis of dendritic cells derived from adherent PBMC cultures.
Figure 3:
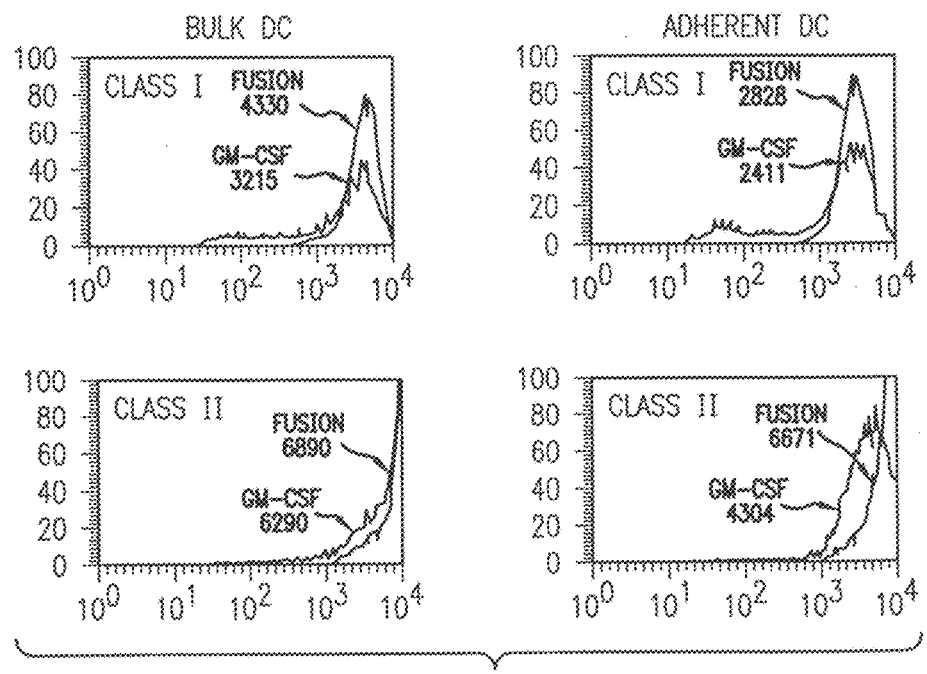
FIG. 3 illustrates upregulation of HLA antigen in dendritic cells by GM-CSF-G250 fusion protein.

FIG. 1 illustrates a RT-PCR analysis of RCC tumor cells. FIG. 2 illustrates FACS analysis of dendritic cells derived from adherent PBMC cultures. FIG. 3 illustrates upregulation of HLA antigen in dendritic cells by GM-CSF-G250 fusion protein. FIG. 4 illustrates cytotoxicity of bulk PMBC modulated by G250-GM-CSF fusion protein (patient 1).

Table 1 shows phenotypic modulation of bulk peripheral blood monocytes by GM-CSF-G250 fusion protein, IL-4, and IL-2 (patient #1).

| Phenotype | Day 7 | Day 21 |
|---|---|---|
| CD3$^+$CD56$^-$ | 60 | 94 |
| CD3$^-$CD56$^+$ | 10 | 3 |
| CD3$^+$CD8$^+$ | 21 | 25 |
| CD3$^+$CD4$^+$ | 40 | 68 |

-continued

| Phenotype | Day 7 | Day 21 |
|---|---|---|
| CD3+TcR+ | 54 | 90 |
| CD3+CD25+ | 10 | 25 |

Table 2 shows phenotypic modulation of bulk peripheral blood monocytes by GM-CSF-G250 fusion protein, IL-4, and IL-2 for patient #2.

| Phenotype | Day 7 | Day 21 | Day 42 |
|---|---|---|---|
| CD3+CD56− | 70 | 90 | 100 |
| CD3−CD56+ | 13 | 1 | 0 |
| CD3+CD8+ | 21 | 22 | 17 |
| CD3+CD4+ | 48 | 74 | 86 |
| CD3+TcR+ | 62 | 91 | 97 |
| CD3+CD25+ | 10 | 28 | 16 |

Example 2

Induction of G250 Targeted and T-Cell Mediated Anti-Tumor Activity Against Renal Cell Carcinoma Using a Chimeric Fusion Protein Consisting of G250 and Granulocyte-Monocyte Colony Stimulating Factor Immunotherapy targeting the induction of a T-cell mediated anti-tumor response in patients with renal cell carcinoma (RCC) holds significant promise. Here we describe a new RCC vaccine strategy that allows for the concomitant delivery of dual immune activators: G250, a widely expressed RCC associated antigen, and granulocyte-macrophage colony-stimulating factor (GM-CSF), an immunomodulatory factor for antigen presenting cells (APC). The G250-GM-CSF fusion gene was constructed and expressed in SF-9 cells using a baculovirus expression vector system. The 66 kDa fusion protein (FP) was subsequently purified through a 6×His-Ni-NTA affinity column and a SP Sepharose/FPLC. The purified FP possessed GM-CSF bioactivity, comparable to that of recombinant GM-CSF when tested in a GM-CSF dependent cell line. When combined with IL-4 (1000 U/ml), FP (0.34 mg/ml) induced differentiation of monocytes (CD14+) into dendritic cells (DC) that express surface marker characteristic for APC. Up-regulation of mature DC (CD83+CD19−) (17% vs 6%) with enhanced HLA class I and class II antigen expression was detected in FP cultured DC as compared to DC cultured with recombinant GM-CSF. Treatment of PBMC with FP alone (2.7 mg/10⁷ cells) augmented both $Th_1$ and $Th_2$ cytokine mRNA expression (IL-2, IL-4, GM-CSF, IFN-γ and TNF-α). When compared to various immune manipulation strategies in the long-term cultures of bulk PBMC, cells treated with FP (0.34 mg/ml) plus IL-4 (1000 U/ml) for one week and then re-stimulated with FP weekly plus IL-2 (20 IU/ml) induced the most growth expansion of T cells expressing T cell receptor (TcR). Moreover, under such immunomodulatory manipulation, RCC specific cytotoxicity that could be blocked by anti HLA class I, anti-CD3 and anti-CD8 antibodies was demonstrated in four out of six tested PBMC cultures. In one tested patient, an augmented cytotoxicity against lymph node (LN) derived RCC target was determined as compared to that against primary tumor targets, which corresponded to an eight-fold higher G250 expression in LN tumor as compared to primary tumor. The replacement of FP with recombinant GM-CSF completely abrogated the selection of RCC specific killer cells. All FP modulated PBMC cultures with antitumor activity showed an up-regulated CD3+ CD4+ cell population. These results indicate that GM-CSF-G250 FP is a potent immunostimulant with the capacity for activating immunomodulatory DC and inducing a T-helper cell supported, G250 targeted, and CD8+ mediated anti-tumor response. These findings have important implications for the use of GM-CSF-G250 FP as a tumor vaccine for the treatment of patients with advanced kidney cancer.

INTRODUCTION

Metastatic renal cell carcinoma (mRCC) poses a therapeutic challenge because of its resistance to conventional modes of therapy such as chemotherapy and radiation therapy (Figlin (1999) *J. Urol.* 61: 381-387). Advances in the treatment of mRCC have evolved significantly in the last decade since the FDA approval of interleukin-2 (IL-2) in 1992. It has become clear that immunotherapy is capable of producing durable remissions in selected RCC patients, yet the overall response rates of immunotherapy remain approximately 25% at best (Fisher et al. (1997) *Cancer J. Sci. Amer.*, 3: S70) at the cost of measurable toxicities to the patient. The recent identification of MHC restricted tumor-associated antigens (TAA) and the understanding of the critical role of immunomodulatory dendritic cells (DC) have provided the rationale for the development of tumor vaccines for cancer therapy (Wang et al. (1999) *J. Mol. Med.*, 77: 640-655; Xu et al. (2000) *Trends in Biotech.* 18: 167-172). Many cancer vaccine strategies have been designed and tested in both animal models and human trials with encouraging results. These include peptide-based vaccines (Rosenberg et al. (1999) *J. Immunol.*, 163: 1690-1695; Parkhurst et al. (1996) *J. Immunol.*, 157: 2539-2548), dendritic cell (DC)-based vaccines (Yang et al. (2000) *J. Immunol.*, 164: 4204-4211; Condon et al. (1996) *Nature Med.*, 2: 1122-1128; Zhou et al. (1996) *Human Gene Ther.*, 10: 2719-2724; Nestle et al. (1998) *Nature Med.*, 4: 328-332; Mulders et al. (1999) *Clin. Cancer Res.*, 5: 445-454), recombinant viruses/DNA/RNA based vaccines (Ulmer et al. (1998) *J Virol.*, 72: 5648-5653; Ying et al. (1999) *Nature Med.*, 5: 823-827; Liu (1998) *Nature Med.*, 4: 515-519), and gene modified tumor cells (Mach et al. (1999) *Cancer Res.*, 60: 3239-3246). Despite that the fact that RCC is thought to be a relatively immunogenic tumor, no RCC associated antigens have been identified and characterized in association with a significant rationale for the development of a kidney cancer targeted tumor vaccine (Gaugler et al. (1996) *Immunogenetics*, 44: 323-330; Brändle et al. (1996) *J. Exp. Med.*, 183: 2501-2508; Brossart et al. (1998) *Cancer Res.*, 58: 732-736).

The first widely expressed RCC tumor associated antigen that contains HLA-A2 restricted CTL epitopes has been recently identified and cloned from a RCC cell line (Grabmaier et al. (2000) *Intl. J. Cancer*, 85: 865-870; Vissers et al. (1999) *Cancer Res.*, 59: 5554-5559). This RCC associated transmembrane protein, designated as G250, has been proven to be identical to MN/CAIX, a TAA expressed in cervical cancer (Opayský et al. (1996) *Genomics*, 33: 480-487). Immunohistochemical staining with mAbG250 revealed that more than 75% of primary and metastatic RCC expressed G250 while little to no expression was detected in the normal kidney (Grabmaier et al. (2000) *Intl. J. Cancer,* 85: 865-870). In addition, G250 expression is found in nearly all clear cell cancers of the kidney, the most common RCC variant, which provides further basis for the use of G250 as a significant immune target for anti-cancer therapy. Antigen presentation is a crucial first step for vaccine-based immunotherapy. We therefore hypothesized that a chimeric protein consisting of G250 and GM-CSF, an immunomodulatory factor for the generation of functional DC, would augment vaccine capacity as compared to the use of either agent alone. Several chimeric fusion proteins containing GM-CSF have been reported and have shown a variety of complex biological effects dependent on their fusion components (Hall et al. (1999) *Leukemia*, 13: 629-633; Tripathi et al. (1999) *Hybridoma* 18: 193-202; Battaglia et al. (2000) *Exp. Hematol.*, 28: 490-498; Batova et al. (1999) *Clin. Cancer Res.*, 5: 4259-4263). GM-CSF has been well characterized as a growth factor that induces the proliferation and maturation of myeloid progenitor cells (Hill et al. (1995) *J. Leukocyte Biol.* 58: 634-642). It enhances macrophage and granulocyte natural cytotoxicity against tumor cells (Parhar et al. (1992) *Europ. Cytokine Network*, 3: 299-306). The function of GM-CSF as a key factor for the differentiation of DC further substantiates its adjutant impact in immune based vaccine therapy (Jonuleit et al. (1996) *Archives of Dermatological Res.* 289: 1-8). Direct evidence of the adjuvant effects of GM-CSF in vaccine based immunotherapy has been demonstrated in animal models. Immunization with tumor peptide at skin sites containing epidermal DC newly recruited by pre-treatment with DNA encoding GM-CSF elicited an antigen specific T cell response, whereas peptide immunization of control skin site showed no immune response (Bowne et al. (1999) *Cytokines Cellu. Mol Ther.*, 5: 217-225). Likewise, treatment of established tumor with a hybridized cellular vaccine generated by fusing GM-CSF gene-modified DC with melanoma cells showed a greater therapeutic efficacy when compared to the treatment with hybridized vaccine generated with non-modified DC (Cao et al. (1999) *Immunol.*, 97: 616-625). An initial Phase I trial further demonstrated that systemic injection of GM-CSF and IL-4 was capable of inducing tumor regression and stable disease response in patients with advanced RCC and prostate cancer (Roth et al. (2000) *Cancer Res.*, 60: 1934-1941). Similarly, vaccination of patients with irradiated autologous RCC or melanoma cells engineered to secrete human GM-CSF also induced a potent anti-tumor immunity (32 Simons et al. (1997) *Cancer Res.* 57: 1537-1546; Soiffer et al. (1998) *Proc. Natl. Acad. Sci., USA*, 5: 13141-13146).

In this example, we describe a strategy to generate fusion proteins (FP) consisting of G250 and GM-CSF. In addition, we tested the feasibility of using this non-viral and non-cellular RCC tumor vaccine as an immunostimulant for the in vitro modulation of DC and induction of G250 targeted anti tumor response in PBMC cultures, that were derived from patients with advanced kidney cancer.

Materials and Methods

Cloning of GM-CSF-G250 Fusion Gene in pVL 1393 Vector

Plasmid p91023(B)-GM-CSF (Wong et al. (1985) *Science* 228: 810-815) was digested with EcoR I, and the 0.8 kb fragment containing the full length of GM-CSF cDNA was used to generate the 0.4 kb GM-CSF fragment containing the functional epitope flanked by an EcoR I site on the 5' side and a Not I site on the 3' side replacing the GM-CSF stop codon, by DNA PCR. The GM-CSF fragment from the PCR product was subcloned into the EcoR I and Bgl II sites of polyhedrin gene locus-based baculovirus transfer vector pVL1393 (Pharmigen, San Diego, Calif.). Similarly, pBM20CMVG250 Osterwick (2000) *Int. J. Cancer*, 85: A65-A70) was used to amplify the full length of G250 cDNA (1.6 kb) containing a Not I site followed by a 6 nucleotide linker coding for 2 arginines by PCR in the 5'-flanking region of the G250 after the removal of its start codon. The 3'-flanking region of G250 was designed to encode 6 histidines followed by the stop codon and Bgl II site. The G250 fragment was gel purified. Both the vector pVL1393 already contained the GM-CSF and the G250 PCR amplified fragments were cut out with Not I and Bgl II. The G250 fragment and the vector were ligated for 3 hr at 16° C., and later transformed and plated on LB plates. The colonies containing the correct plasmid were purified by cesium chloride buoyant ultracentrifugation. The plasmid was cut with a set of different restriction enzymes to verify the plasmids. The plasmid clones were further verified for histidine tag using an Amplicycle Sequencing Kit (Perkin Elmer).

Generation and Purification of Fusion Protein

The recombinant baculovirus containing His-tagged GM-CSF-G250 fusion gene was generated by co-transfection of 0.5 mg BaculoGold DNA (modified AcNPV baculovirus DNA) (Pharmigen, San Diego, Calif.) and 5 mg of pVL1393/GM-CSF-G250 in 519 cells (*Spodoptera frugiperda*). Viruses were further amplified at a low MOI (<1) in adherent Sf9 insect cells and the titers of the virus were determined by plaque assay. Expression of GM-CSF-G250 FP in Sf9 cells was determined by immunocytochemical analysis using anti-G250 mAb, anti-GM-CSF antibody (Genezyme, Cambridge, Mass.) and irrelevant Ab. Sf9 cells infected with pVL1392-Xy1E recombinant virus (Pharmigen) and uninfected SD cells were used as negative control for FP expression and analysis. The viruses used for protein production were isolated and amplified from a single plaque. Cell lysate was prepared from the SD cells infected with viruses at MOI of 5 for three days with insect cell lysis buffer containing protease inhibitor cocktail (Pharmigen, San Diego, Calif.). Filtered lysate (0.22 mm filter) was applied to a $Ni^{2+}$-NTA agarose column with high affinity for 6×His (Qiagen, Santa Clarita). After extensive washing of the column (50 mM Na-phosphate, 300 mM NaCl, 10% glycerol, pH 8.0), the fusion protein was eluted stepwise column (50 mM Na-phosphate, 300 mM NaCl, 10% glycerol, pH 6.0) by increasing concentration of imidazole from 0.1M up to 0.5M. All purification steps were carried out at 4° C. Fractions were analyzed by Western blot using anti-GM-CSF antibody. The peak fractions were combined, dialyzed and re-applied to an $Ni^{2\pm}$-NTA agarose column for repeated purification. Fractions containing FP were pooled, dialyzed and further applied to a FPLC column containing SP Sepharose, High Performance (Amersham Pharmacia Biotech, Piscataway, N.J.). Fusion protein was eluted with an increasing salt gradient from 50 mM to 1M NaCl in buffer X (20 mM Tris, 1 mM EDTA, 10% Glycerol) and the fractions containing FP were pooled, dialyzed and sterilized through 0.2 m filter. The Coomassie blue and silver stains were used to analyze the purity of GM-CSF-G250 fusion protein. The protein concentration was determined by Bio-Rad Dc Protein Assay (Bio-Rad, Hercules, Calif. 94547).

GM-CSF Dependent Proliferation Assay

The biological activity of the GM-SF component of the FP was determined by measuring the proliferation of GM-SF dependent TF-cells (Kitamura et al. (1989) *J. Cellu. Physiol.*, 140: 323-334) in the presence of FP. TF-1 cells were seeded in 96-well plates in triplicate in culture medium (RPMI medium+10% FBS) at the concentration of $2\times10^4$ cells/well containing titrated concentration of FP or the corresponding amount of recombinant human GM-CSF (rh- GM-CSF). Cultures were incubated for 5 days and $^3$H thymidine (0.1 mCi/well) was added 12 h prior to harvest. The incorporated $^3$H-thymidine was measured by scintillation counting with a β counter.

Phenotypic Analysis of DC by Fluorescence Activated Cell Sorting (FACS)

The phenotype of DC generated from both adherent and bulk PBMC was determined by two-color immunofluorescence staining as described in Hinkel et al. (2000) *J. Immunother.*, 23: 83-93. Both adherent PBMC and non-fractionated bulk PBMC were cultured with 1000 U/ml of IL-4 plus either GM-CSF (800 U/ml) or FP (0.34 mg/ml) for 7 days and the identity of DC was determined. Cell cultures (1×10$^5$ cells) were re-suspended in 50 ml FACS buffer (PBS, 2% new born calf serum, 0.1% sodium azide) and incubated with 10 ml of the appropriate fluorescein isothiocyanate (FITC) or phycoerythrine (PE) labeled monoclonal antibodies for 30 min at 4° C. After staining, cells were washed twice with PBS and re-suspended in 200 ml FACS buffer plus 200 ml paraformaldehyde 2%. Five to ten thousand events per sample were acquired on a Becton-Dickinson FACScan II flow cytometer that simultaneously acquires forward (FSC) and side scatter (SSC), as well as FL1 (FITC) and FL2 (PE) data, and analyzed utilizing the CellQuest Software (Becton-Dickinson, San Jose, Calif.).

Settings for all parameters were optimized at the initiation of the study and were maintained constant throughout all subsequent analyses. DC population in bulk PBMC culture was gated based on their size and granularity. In all samples the position of quadrant cursors was determined by setting them on samples stained with the appropriated isotype control antibody. The following antibodies were employed for characterization of the DCs phenotype: Anti-CD86 (B7-2; PharMingen, San-Diego, Calif.), Anti-CD40 (Caltag, Burlingame, Calif.), anti-HLA class I (W6/32, ATCC HB95), anti-HLA-DR (Immunocytometry System; Becton Dickinson, Mountain View, Calif.), anti-CD14 (Catlag laboratories, San Francisco, Calif.) and isotype control IgG1/IgG2a (Beckton Dickinson). The CD83$^+$ surface marker was used to delineate the maturation of DC. In order to discriminate DC (CD83$^+$CD19$^-$) from activated B cells (CD83$^+$CD19$^+$), dual color staining utilizing CD19FITC and CD83PE (Immunotech, Marseille, France), was performed.

Semi-Quantitative Reverse Transcriptase-Polymerase Chain Reaction (RT-PCR) Analysis of Cytokine Profile in PBMC.

Total RNA was extracted from PBMC treated with FP (2.7 mg/10$^7$ cells) for various time intervals up to 24 hr at 37° C., using acid guanidine isothiocyanate-phenol-chloroform extraction. Reverse transcription of messenger RNA into cDNA was carried out by incubating titrated RNA with AMV reverse transcriptase, primer oligo (dT), dNTP, and RNAse inhibitor at 42° C. for 1 hour. One ml of each cDNA sample was amplified utilizing PCR in a total volume of 25 ml, (30 ng [$^{32}$P]-5'-oligonucleotide, 100 ng 3'-oligonucleotide primer, 2.5 ml modified 10×PCR buffer, 1.25 units Taq polymerase, and autoclaved double distilled water to a volume of 25 ml). The PCR mixture was amplified for 25 cycles in a DNA Thermocycler (Perkin-Elmer, Norwalk, Conn.). Each cycle consisted of denaturation at 94° C. for one minute and annealing/extension at 65° C. for 2 minutes. The 32P-labeled PCR products were then visualized directly via acrylamide gel electrophoresis and autoradiography and then quantitated by excision of bands and subsequent scintillation counting.

The signal intensity of each amplified product was calibrated to its corresponding β-actin mRNA expression as an internal control for quantitation of expression levels. In addition, quantitative analysis was further elucidated by a serial dilution of mRNA (1:3, 1:10, 1:30 and 1:300) and co-amplification of β-actin and GM-CSF mRNA. The sequences of the oligonucleotide primer pairs are as follows: β-actin: 5'-CAA CTC CAT CAT GAA GTG TGA C-3' (SEQ ID NO:11), 3'-CCA CAC GGA GTA CTT GCG CTC-5' (SEQ ID NO:12); GM-CSF: 5'-CCA TGA TGG CCA GCC ACT AC-3' (SEQ ID NO:13), 3'-CTT GTT TCA TGA GAG AGC AGC-5' (SEQ ID NO:14); TNF-α: 5'-TCT CGA ACC CCG AGT GAC AA-3' (SEQ ID NO:15), 3'-TAC GAC GGC AAG GAT TAC ATC-5' (SEQ ID NO:16); IFN-γ: 5'-ATG AAA TAT ACA AGT TAT ATC TTG GCT TT-3' (SEQ ID NO:17), 3'-ATG CTC TTC GAC CTC GAA ACA GCA T-5' (SEQ ID NO:18); IL-2: 5'-GGA ATT AAT AAT TAC AAG AAT CCC-3' (SEQ ID NO:19), 3'-GTT TCA GAT CCC CTT TAG TTC CAG-5' (SEQ ID NO:20); IL-4: 5'-CTT CCC CCT CTG TTC TTC CT-3' (SEQ ID NO:21), 3'-TTC CTG TCG AGC CGT TTC AG-5' (SEQ ID NO:22).

Immunomodulation of PBMC with Fusion Protein

Fresh isolated PBMC from patients with RCC expressing G250 were cultured in RPMI 1640 medium supplemented with 10% autologous serum. Various schedules of immunomodulatory protocols of PBMC cultures with FP were carried out as described in Table 3 and FIG. 10. The growth of PBMC was determined by cell count, and the cytolytic activity of PBMCs was assayed for different targets in a prolonged 18-hour chromium-51 (51Cr) release assay. Five thousand 51 Cr-labeled target cells per well were seeded in a 96-well microtiter plate (Costar, Cambridge, Mass.) and mixed with PBMC yield several E/T ratios (40:1, 20:1, 10:1, and 5:1). Cytotoxicity was expressed as lytic units (LU) per 10$^6$ effector cells with lytic unit being defined as the number of effector cells that induce 30% lysis. T cell mediated and RCC specific cytotoxicity was confirmed by blocking assays in which targeted autologous tumor cells were pretreated with anti-human leukocyte antigen (HLA) class I, class II, or PBMC were pretreated anti-CD3, anti-CD4, anti-CD8, or isotype control antibody (Becton Dickinson) for 30 min at 4° C., before addition of cells to cytotoxicity culture plates. Spontaneous release of all targets was equal or less than 20% of maximal release of 51-Cr release. The following target cells were used: autologous normal kidney cells (G250−), autologous RCC tumor cells (G250+), allogeneic RCC cells (G250+), allogeneic prostate cells (CL-1), and human fibroblast (hFb).

TABLE 3

Phenotypic Modulation of Bulk PBMC by Fusion Protein (FP)

| Phenotype | Pre-cultured | IL-2 | IL-2 + FP | IL-2 + IL-4 + FP IL-2 + FP | FP IL-2 + FP | FP + IL-4 IL-2 + FP |
|---|---|---|---|---|---|---|
| CD56$^+$CD3$^-$ | 25 | 13 | 11 | 4 | 9 | 1 |
| CD5$^-$CD3$^+$ | 46 | 47 | 70 | 84 | 88 | 94 |
| CD4$^+$CD8$^-$ | 31 | 28 | 39 | 42 | 66 | 46 |

TABLE 3-continued

Phenotypic Modulation of Bulk PBMC by Fusion Protein (FP)

| Phenotype | Pre-cultured | IL-2 | IL-2 + FP | IL-2 + IL-4 + FP IL-2 + FP | FP IL-2 + FP | FP + IL-4 IL-2 + FP |
|---|---|---|---|---|---|---|
| CD4$^+$CD8$^+$ | 3 | 10 | 20 | 29 | 4 | 28 |
| CD4$^-$CD8$^+$ | 22 | 24 | 31 | 24 | 22 | 25 |
| CD3$^+$TcR$^+$ | 40 | 45 | 72 | 69 | 79 | 96 |
| CD3$^+$CD25$^+$ | 19 | 43 | 61 | 54 | 17 | 86 |

Results

Generation of GM-CSF-G250 Fusion Protein from Baculovirus-Infected SF-9 Cells.

Baculovirus expression technology and the 6xHis affinity purification system were used to generation GM-CSF-G250 FP as described above. The success of gene cloning and generation of recombinant baculovirus was verified by the immunohistochemical staining of viruses infected Sf9 cells using anti GM-CSF and anti-G250. Abundant G250 and GM-CSF protein expression were detected in Sf-9 cells that were infected with GM-CSF-G250 recombinant baculoviruses (FIG. 6A, top and middle panel), whereas no expression of GM-CSF or G250 was detected in non-infected cells (FIG. 6A, bottom panel) or cells infected with pVL1392-Xy1E recombinant viruses (data not shown). Western blot analysis was used to evaluate the efficiency of 6xHis affinity tag in FP for Ni$^{2+}$-NTA agarose. An expected 66-kDa band which detected with anti-GM-CSF appeared in the fractions collected from number 5 to number 25 with the peak concentration at fraction 15 to 19 (FIG. 6B). The protein purity was further improved by re-run of positive fractions through Ni$^{2+}$-NTA agarose column and subjected to FPLC using SP Sepharose column. A major single 66 kDa band was detected in SDS-PAGE analysis stained with coomassie blue (FIG. 6C).

Purified GM-CSF-G250 Fusion Protein Retained GM-CSF Bioactivity

Figure 7A:
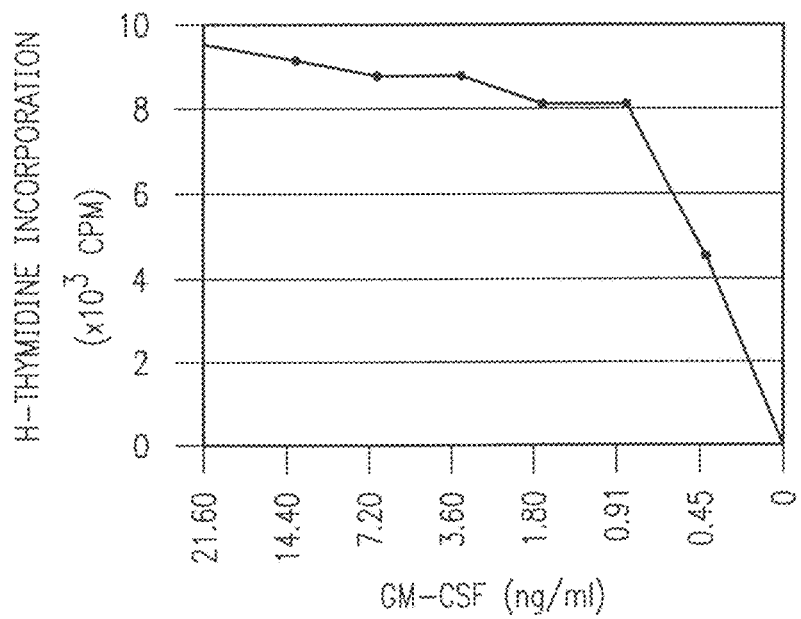
FIGS. 7A and 7B show a comparison of functional activity of recombinant GM-CSF and purified GM-CSF-G250 fusion protein. GM-CSF activity was measured using the GM-CSF dependent human cell line, TF-1. The TF-1 cells (2×104/well/ml) were cultured in the presence of serially diluted amount of (FIG. 7A) recombinant GM-CSF or, (FIG. 7B) purified GM-CSF-G250 fusion protein as indicated. After a 5-day incubation the cultures were pulsed with 0.1 mCi tritiated thymidine for an additional 12 h. The cultures were then harvested and the incorporated thymidine measured by scintillation counting.
Figure 7B:
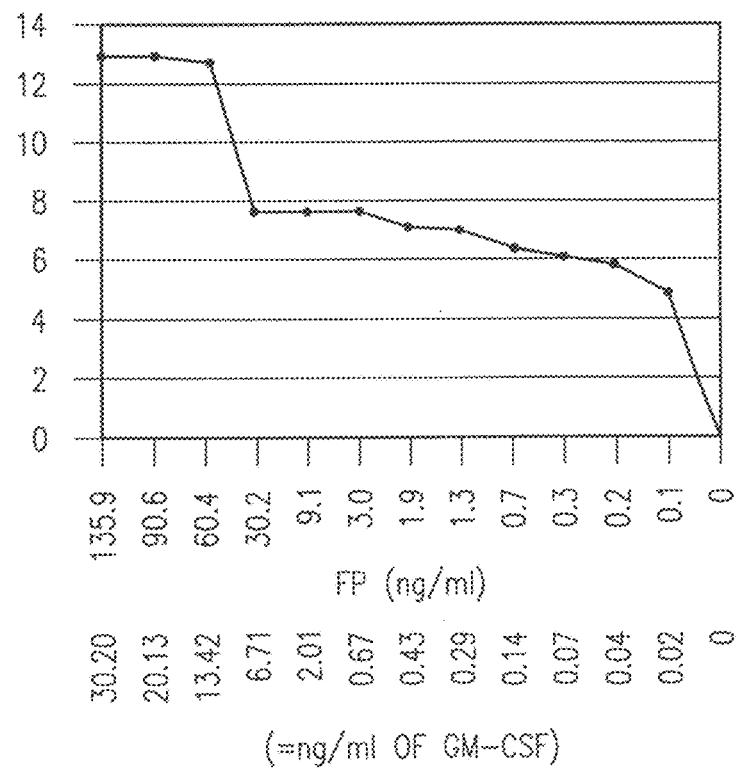

To determine whether the bioactivity of the GM-CSF was preserved in the purified FP, the FP was analyzed for its ability to support the proliferation of a GM-CSF dependent cell line, TF-1. Serial dilutions of FP were performed to span the effective concentration range. The experiments were conducted in parallel with recombinant GM-CSF. The results from the $^3$H-thymidine incorporation assay demonstrated that the FP could stimulate TF-1 cell growth with a biphasic dose dependent manner (FIG. 7B). When compared to recombinant GM-CSF (FIG. 7A), comparable bioactivity was determined in the presence of FP with equivalent concentrations of GM-CSF in the range between 0-6.71 ng/ml (=0-30.2 ng/ml FP). In the presence of concentrations higher then 30.2 ng/ml of FP, the growth induction of TF-1 by FP exceeded the growth induction by recombinant GM-CSF by 1.3 fold (FIG. 7A, 7B).

Figure 8A:
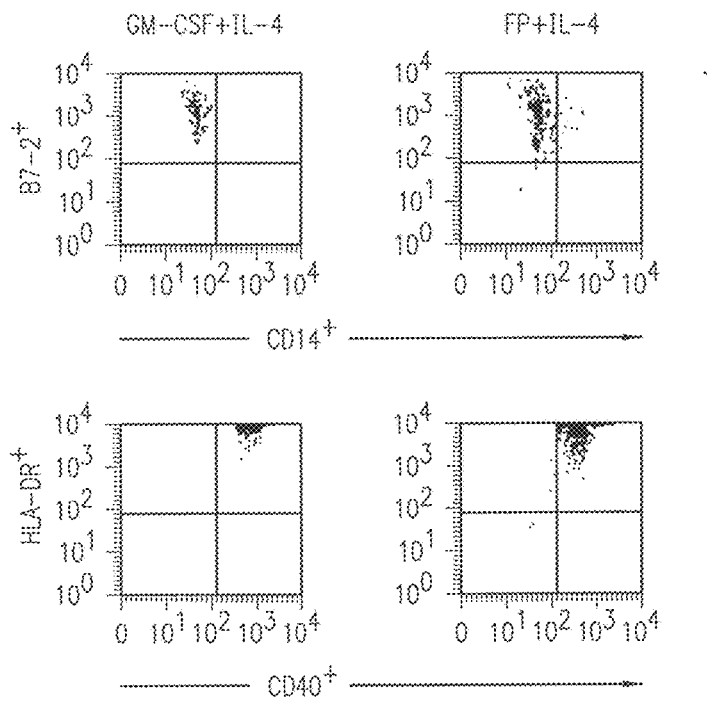
FIGS. 8A, 8B, and 8C show the immunomodulatory effects of fusion protein on dendrtic cells.
Figure 8B:
Figure 8C:
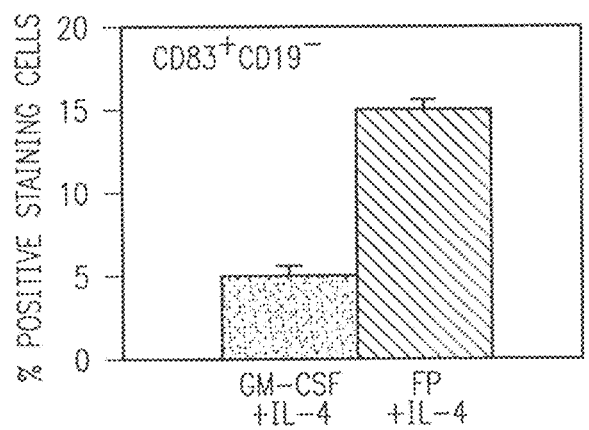

Immunomodulatory Effect of Fusion Protein on Antigen Presenting Cells in PBMC Culture In order to study how the FP could affect the development of DC, PBMC derived from patients with RCC were cultured in the presence of FP (0.34 mg/ml) plus IL-4 (1000 U/ml) for 7 days and compared to that cultured in GM-CSF (800 U/ml) plus IL-4. FACS analysis revealed a high percentage of large granulocytes expressing B7-2$^+$, CD40$^+$ and HLA-DR$^+$ in both conditions whereas CD14$^+$ cells were negligible (FIG. 8A). However, when compared to dendritic cells cultured with recombinant cytokines, an enhanced expression of both HLA class I (mean relative linear fluorescence intensity=4830 vs 3215) and HLA class II (6890 vs 6290) was detected in the FP modulated DC cultures (FIG. 8B). In addition, there was a three-fold increase of mature DC (CD83$^+$CD19$^-$) in FP modulated DC cultures (FIG. 8C). This observation was consistent in several bulk PBMC cultures derived from RCC patients (n=3) and healthy donors (n=2). Similar FP mediated immunomodulatory profile was also determined on conventional adherent DC cultures (data not shown). A lower efficiency of DC differentiation was observed when DC were cultured in the presence of FP alone without IL-4. A mix of CD14$^+$ and CD14-B7-2$^+$ cell population were determined on day 7 (data not shown).

Fusion Protein Induces Activation of Cytokine Genes in PBMC

Figure 9:
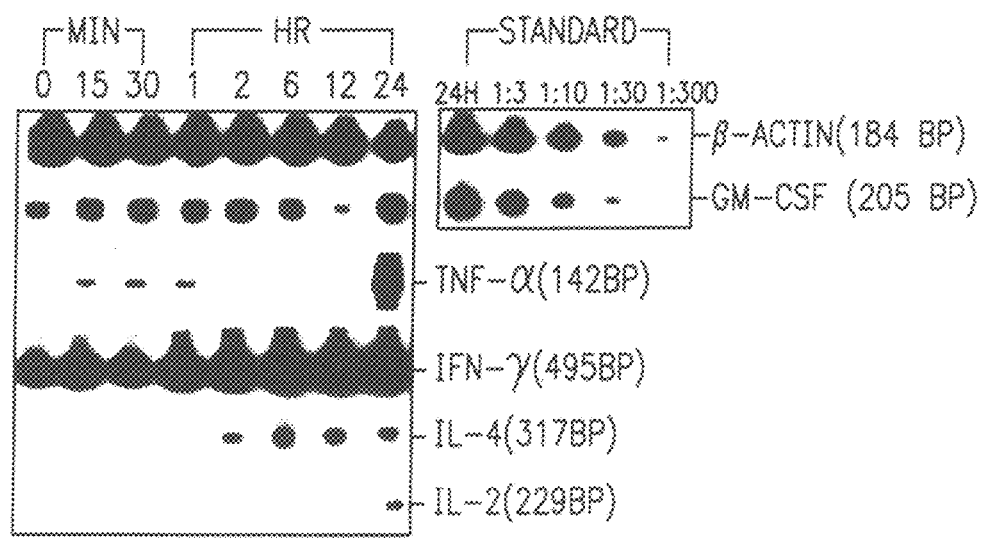
FIG. 9 shows a time course of cytokine mRNA expression in PBMC that were treated with GM CSF G250 fusion protein (FP) (2.7 mg/107 cells) for various time period as indicated and then harvested for semi-quantitative RT-PCR analysis. The 32P-labeled PCR products were separated by electrophoresis through a 7% acrylamide gel. Gels were dried and subjected to autoradiography. Titrated standard was prepared from diluted RNA samples extracted from PBMC treated with FP for 24 h.

To identify whether the fusion protein has a direct effect on the regulation of cytokine genes in PBMC, freshly isolated PBMC cells, derived from RCC patients, were treated with FP alone (2.7 mg/10$^7$ cells). The kinetics of cytokine gene activation was followed by analysis of multiple cytokine mRNA expression through time course as indicated in FIG. 9. When compared to untreated PBMC, treatment of uncultured PBMC with FP gradually enhanced GM-CSF, TNF-α, IFN-γ, IL-4, IL-2 mRNA expression with the peak level at 24 hr post treatment except IL-4. The peak of IL-4 mRNA expression was detected at 6 hr after the treatment (FIG. 9).

Figure 10A:
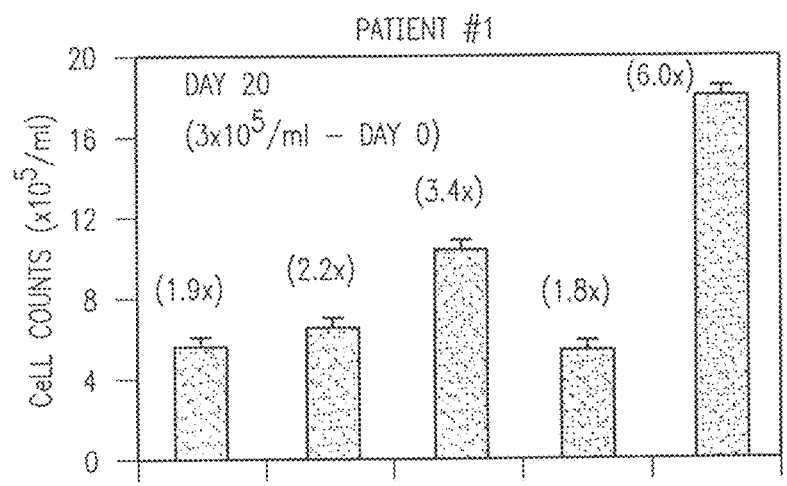
FIGS. 10A, 10B, 10C, and 10D show growth and cytotoxicity profiles of patient-derived PBMC stimulated with GM-CSF-G250 fusion protein.
Figure 10B:
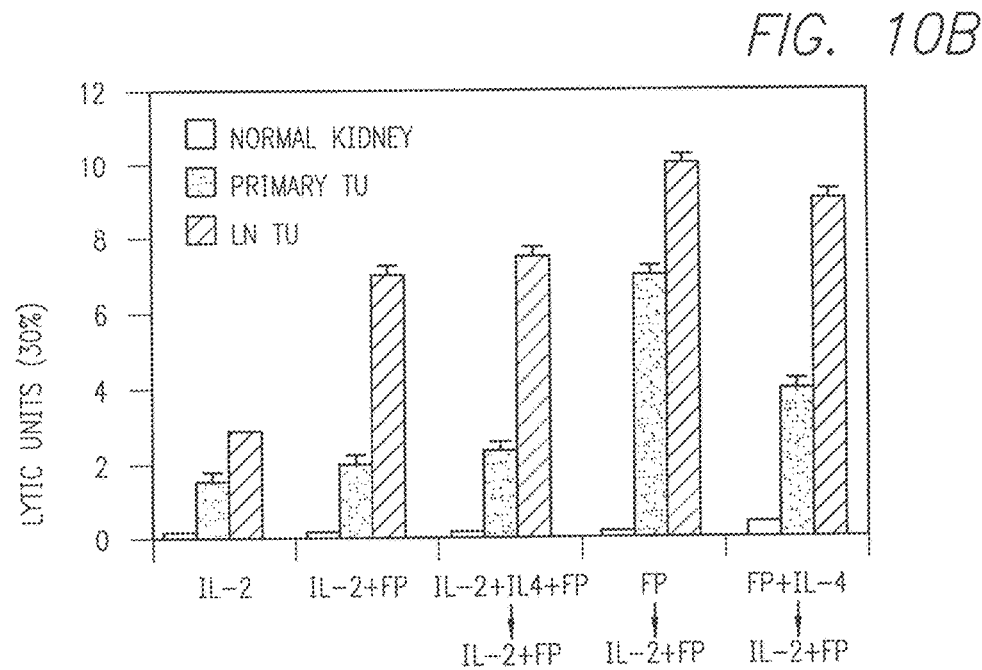
Figure 10C:
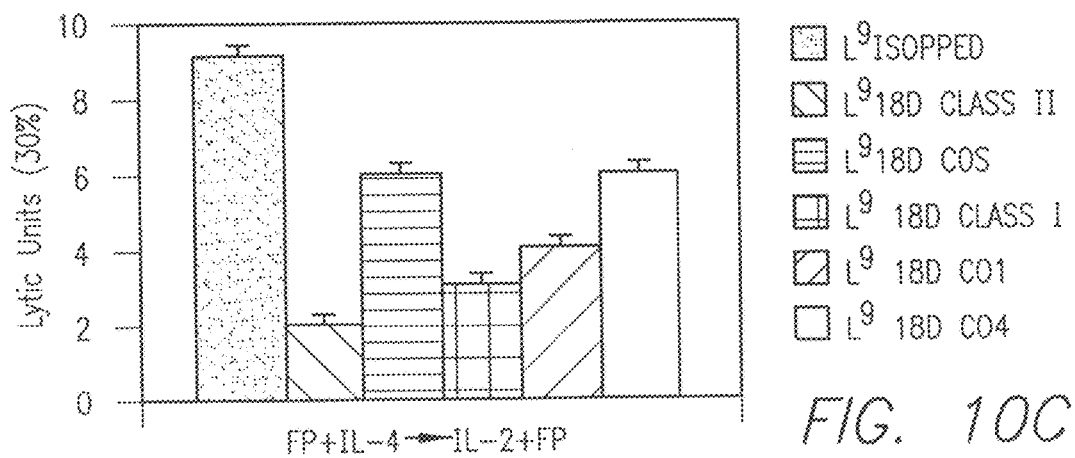
Figure 10D:
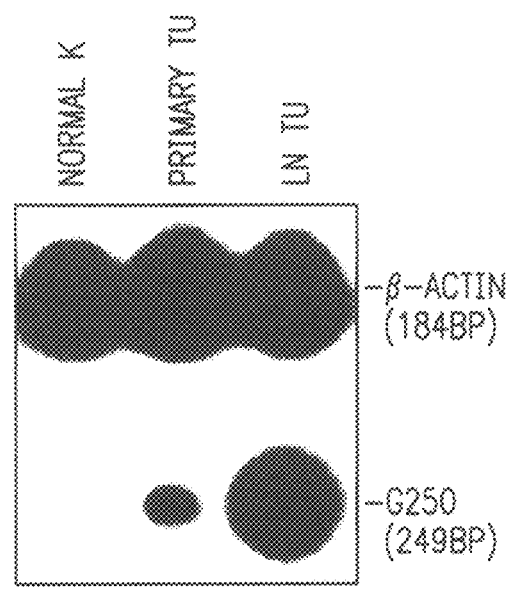

Fusion Protein Induces T Cell Mediated and G250 Targeted Immune Response in PBMC Cultures Five immunomodulatory protocols with and without FP were tested and compared in PBMC cultures. These culture conditions included 1) IL-2 alone (40 IU/ml), 2) IL-2+FP (0.34 mg/ml)(re-stimulated weekly), 3) IL-2+IL-4 (1000 U/ml)+FP for one week then restimulated with FP+IL-2, 4) FP alone for one week then restimulated with FP+IL-2 and 5) FP+IL-4 for one week then re-stimulated with IL-2+FP. As indicated in FIG. 10 (patient #1), among various immunomodulatory treatments tested, the condition with pre-treated PBMC with FP plus IL-4 for one week and subsequently restimulated with IL-2 (40 ILT/ml) and FP weekly, showed the highest growth expansion (6.0x) (FIG. 10A). A similar growth profile with enhanced growth activity in this particular condition was determined in another 3 PBMC cultures that were derived from patients with RCC. In one particular patient (patient #11 who had a positive lymph node (LN), an enhanced cytotoxicity against LN derived tumor target was determined in all four FP modulated PBMC cultures (3 cycles of re-stimulation) when compared to the cytotoxicity against primary tumor target (FIG. 10B). Notably, this enhanced killing activity corresponded to an eight-fold increase of G250 mRNA expression in LN derived RCC tumor, as determined by a semi-quantitative RT-PCR, when compared to primary RCC cells (FIG. 10C). When LN tumor target cells were pretreated with anti HLA class I (77%) or alternatively, effectors were pretreated with anti CD3 (66%) or anti CD8 (55%) prior to the assay, RCC targeted cytotoxicity was markedly reduced. Whereas anti HLA class II (33%) or anti CD4 (33%) treatment could lead only to a lesser inhibition of cytotoxicity (FIG. 10C). Although poor growth expansion (1.8×) was detected in the condition that pretreated PBMC with FP alone for one week and re-stimulated with 1L-2 plus FP, the highest cytotoxcity against both primary and LN derived RCC target was detected when compared to other tested conditions (FIG. 10B).

To identify the phenotypic identity of FP modulated PBMC that possess anti-tumor activity, phenotypic analysis was performed on the day when cytotoxicity was determined. A markedly increased T cell population (70-94%) expressing T cell receptor (72-96%) was detected in all FP stimulated PBMC cultures, when compared to pre-cultured PBMC (46%) or PBMC cultured with IL-2 alone (47%) (Table 3). Notably, the T cell population expressing the most IL-2 receptor ($CD3^+CD25^+$) (86%) was determined to occur in the condition that pretreated cells with FP plus IL-4 prior to re-stimulation with IL-2 and FP. This also corresponded to the greatest growth expansion in T cell population when compared to all other tested immunomodulatory protocols (FIG. 10A). Correspondingly, PBMC that were pretreated with FP for one week demonstrated a minimal T cell population expressing the IL-2 receptor (19%) and demonstrating the least growth expansion (Table 3 and FIG. 10A).

Figure 11A:
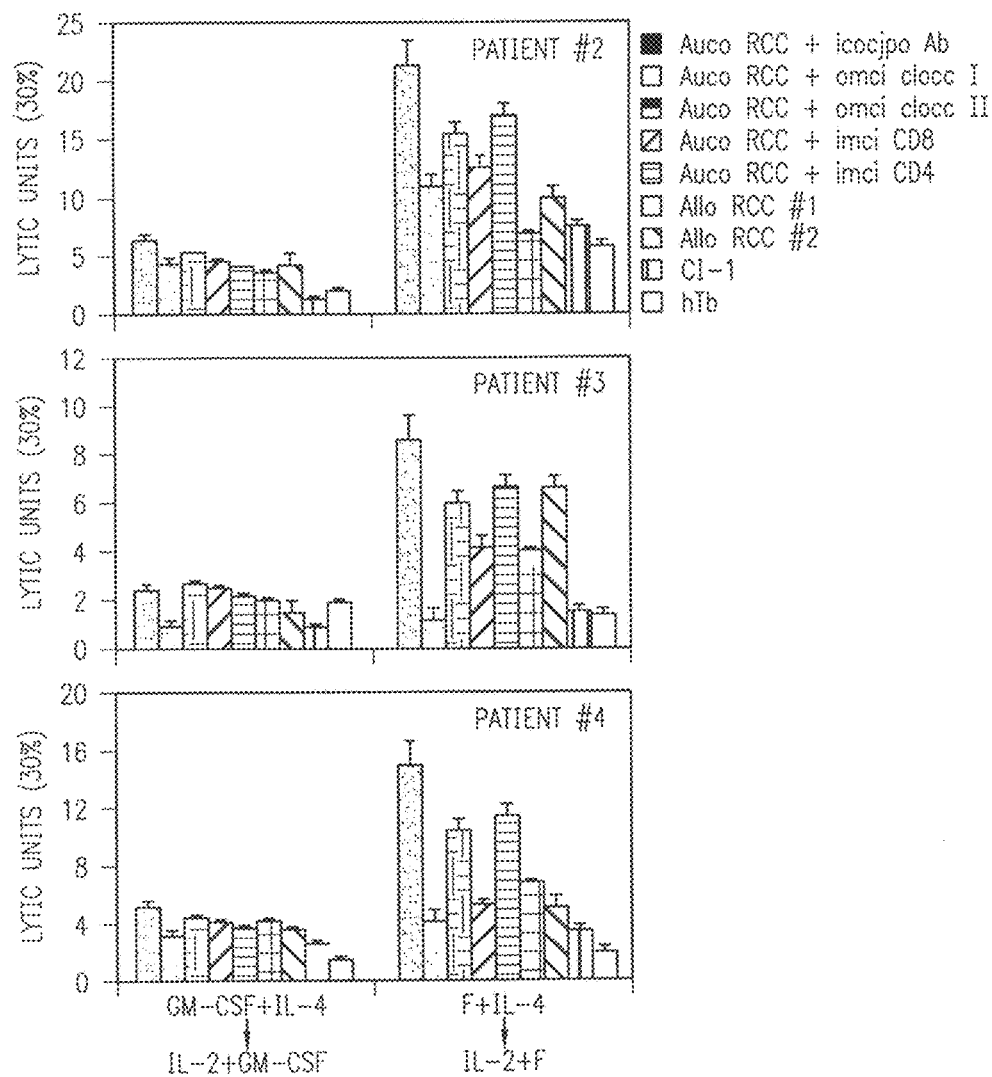
FIGS. 11A and 11B shows fusion protein induced G250 targeted and MHC restricted T cell immunity.
Figure 11B:
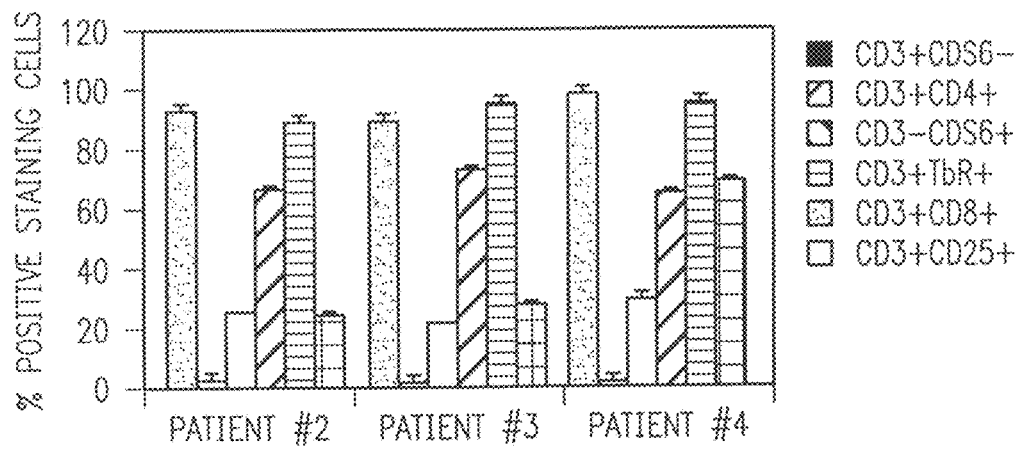

Replacement of FP with GM-CSF Abrogates the Selection of RCC Targeted Cytotoxic T Cells In order to confirm that the component of G250 in the FP is the determinant for the growth selection of CTL against RCC, cytotoxicity assay was performed with PBMC that were cultured in the presence of GM-CSF and IL-4 for one week then continuously restimulated with IL-2 and GM-CSF (800 U/ml). Minimal cytotoxicity against autologous RCC was determined in all tested PBMC cultures without FP stimulation. Whereas the corresponding PBMC cultures stimulated with FP showed an MHC restricted, T cell mediated cytotoxicity against autologous RCC (FIG. 11A) that expressed high level of G250 (data not shown). Predominant $CD3^+CD4^+$ cell population was detected in all three FP modulated PBMC cultures (68%, 74%, and 66%) that expressed antitumor activity, when compared to $CD3^+CD8^+$ cell population (25%, 22%, and 30%) (FIG. 11B). Moreover, both Th1 and Th2 cytokine mRNA were detected in these FP modulated PBMC cultures which included GM-CSF, TNF-α, IFN-γ, IL-2 and EL-4 (data not shown).

Discussion

Renal cell carcinoma (RCC) is responsive to immunotherapy. However, it is believed that no immune-based treatment protocol has been previously shown that would effectively eradicate tumor lesions in the majority of patients. It is believed that means of immune strategy, the type of immune activators used, the method of administration, and the pretreatment immune status of patients all could influence the ultimate immune response in cancer patients that are treated with immune-based therapy. Therefore, an important issue for an effective cancer vaccine is the development of a potent adjuvant that can facilitate both induction and augmentation of an immune response with antitumor activity. To achieve this, we proposed a chimeric construct consisting of G250 and GM-CSF. The demonstration of G250 expression in SF-9 cells and GM-CSF bioactivity in the purified 66 kDa band of protein molecule confirmed the efficacy of the gene construct and the effectiveness of the selected protein purification method.

Antigen presentation by DC is important, not only for the induction of primary immune responses, but may also be important for the regulation of the type of T cell-mediated immune response (Banchereau et al. (2000) *Ann. Rev. Immunol.*, 18: 767-811). We recently developed a non-fractionated bulk PBMC culture system for the study of the maturation and immunomodulatory function of $CD14^+$ derived DC and the interaction between the DC and co-cultured lymphocytes (Hinkel et al. (2000) *J. Immunother.*, 23: 83-93). Using this system, antigen loading can be performed during the early culture period of PBMC in the presence of GM-CSF and IL-4, when immature DC/monocytes can take up and process tumor antigen. As we have previously demonstrated that DC modulated co-cultured lymphocytes in bulk PBMC culture can be further expanded to CTL by repetitive stimulation with low dose IL-2 and RCC tumor lysate. Likewise, direct treatment of bulk PBMC with IL-4 and FP not only induced the differentiation of $CD14^+$ cells into DC but also increased the maturation of DC when compared to DC generated in IL-4 and GM-CSF. This suggests that signaling pathway in DC maturation can be induced by FP stimulation (Rescigno et al. (1998) *J. Exp. Med.*, 188: 2175-2180). Moreover, when compared to recombinant GM-CSF, upregulated HLA antigen expression was determined on FP modulated DC further indicating that DC are capable of internalizing, processing, and presenting FP through HLA antigens in DC. Whether the G250 was taken up by APC through GM-CSF receptor internalization or via the G250 component remains to be determined.

It appears that preincubation of PBMC with FP and IL-4 prior to exposing IL-2 facilitates a better effector expansion. This may be explained if exogenous IL-4 could synergize the FP for the mobilization of DC differentiation and maturation and subsequent presentation of the antigen peptides to the surrounding immune cells. Although a successful CTL selection also could be achieved by other tested immunomodulatory protocols with FP, the growth expansion of CTL was not favorable. This may be partly associated with a "delayed" DC differentiation under the sub-optimal concentration of IL-4 (note: FP can induce IL-4 secretion by PBMC). Moreover, pre-exposure of IL-2 to a non-antigen stimulated PBMC usually results in the expansion of non-specific lymphokine activated killer cells with short-term killing activity (Roussel et al. (1990) *Clin. Exp. Immunol.*, 82: 416-421). Recently, Huang et al. (1994) *Science*, 264: 961-965, demonstrated that even "immunogenic" tumors, such as those modified to express co-stimulatory molecules, fail to stimulate the immune system, unless functional APC are available to process and present the antigens. It thus appears that the most effective anti cancer vaccine strategy should target manipulation of enhancing T cell priming at the level of APC in patients.

That the replacement of FP with equivalent dose of recombinant GM-CSF abrogated the selection and propagation of RCC specific CTL suggests that activation and propagation of CTL is antigen (G250)-dependent. Whereas the GM-CSF has served as an effective adjuvant for antigen presentation and amplification of T cell activity including cytokine response (Mach et al. (1999) *Cancer Res.*, 60: 3239-3246; Pulendran et al. (1999) *Proc. Natl. Acad. Sci., USA*, 96: 1036-1041). Although FP induced G250 targeted antitumor activity is mainly mediated by $CD8^+$ T cells, a predominant up-regulation of $CD4^+$ T cells was detected in most cultures. The FP mediated Th1 and Th2 cytokine release and enhancement of HLA class II expression in DC cells further suggests FP mediated antitumor immunity may involve the priming of both $CD4^+$ and $CD8^+$ T cells specific for G250. The role of CD4+ T helper cells in this response may be attributed to provide regulatory signals required for that priming of MEW class I restricted CD8+ CTL (Mach et al. (1999) *Cancer Res.*, 60: 3239-3246).

Studies comparing the efficacy of various formulations of tumor vaccines in parallel demonstrated that the use of DC transfected with DNA coding for TAA is superior to peptide-pulsed DC and naked DNA based vaccine for eliciting both antigen-specific CD8 and CD4 T cell response (Yang et al. (1999) *Intl. J. Cancer*, 83: 532-540). This observation indicates that computer predicted peptides might not be naturally processed and presented on the tumor cells surface for the recognition by peptide reactive T cells. Thus, some in-vitro peptide-reactive T cells could only lyse peptide pulsed cell targets but not tumor cells expressing the entire tumor antigen (Vissers et al. (1999) *Cancer Res.*, 59: 5554-5559; Rammensee et al. (1993) *Annual Rev. Immunol.*, 11: 213-244). Likewise, a peptide-based vaccine could effectively elicit expansion of vaccine specific T cells in PBMC of cancer patients, but such response was not associated with a clinical tumor regression (Lee et al. (1999) *J Immunol*, 163: 6292-6300). Therefore, immunization with the current construct of whole G250 antigen may have the advantage over the peptides for the presentation of multiple, or unidentified epitopes in association with MHC class I and class II molecules by APC. On the basis of the potency and specificity of the GM-CSF-G250 fusion protein in the activation of G250-reactive T cells with antitumor activity, our data indicate that vaccination with GM-CSF-G250 FP will provide therapeutic impact for the treatment of advanced kidney cancer.

Example 3

Figure 12:
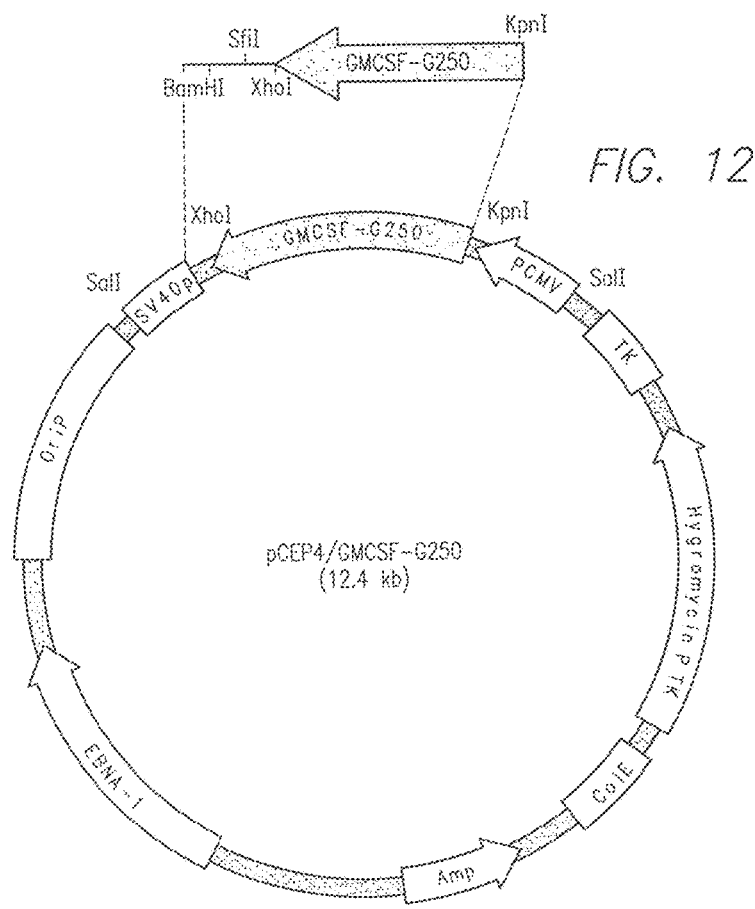
FIG. 12 shows a map of the vector pCEP4/GMCSF-G250 where the recombinant gene is inserted between KpnI and XhoI.
Figure 13:
FIG. 13 digestion and electrophoresis of pCEP4/GMCSF-G250 Lane 1: pCEP4/GMCSF-G250. Lane 2: pCEP4/GMCSF-G250 digested with KpnI and XhoI. M: Molecular weight marker (1 kb PLUS DNA ladder (Gibco)

Generation of the Mammalian Expression Vector pCEP4-GMCSF-G250 i) Amplification of the Recombinant Gene GMCSF-G250 without the His Tag and Cloning into pGEM-T.

pVL1393-GMCSF-G250 (His tag) was used as a template in a PCR reaction that was carried out using primers designed to introduce a KpnI before the start codon of the GMCSF (5' primer) and a XhoI site after the stop codon (3' primer). In addition, the 3' primer was designed to eliminate the poly-Histidine coding sequence previously introduced for detection and purification purposes. A high fidelity amplification system (Expand High Fidelity System, Boehringer-Mannheim) was used to avoid mutations in the PCR product, which was directly cloned into pGEM-T vector (Promega), a convenient vector for further sequencing and cloning steps, resulting in pGEMT-GMCSF-G250. Completely sequencing of the GMCSF-G250 gene revealed no mutation and the expected absence of the poly-histidine coding sequence.

ii) Cloning of the GMCSF-G250 into the Mammalian Expression Vector pCEP4.

pCEP4 is an episomal vector mammalian expression vector that uses the cytomegalovirus (CMV) immediate early enhancer/promoter for high level transcription of recombinant genes inserted into the multiple cloning sites and also carries the hygromycin B resistance gene for stable selection in transfected cells. Subcloning of GMCSF-G250 into pCEP4 was carried out with a digestion of vectors pGEMT-GMCSF-G250 and pCEP4 with restriction enzymes KpnI and XhoI and further gel purification and ligation of the resulting linearized pCEP4 and GMCSF-G250. The new plasmid pCEP4-GMCSF-G250 (FIG. 12) contained the recombinant gene in the proper orientation as expected. A SalI digestion of pCEP4-GMCSF-G250 released the complete expression cassette CMV promoter-gene-polyadenylation signal (3.7 kb, FIG. 13) that can be cloned into the E1 and E3 deleted adenovirus or gutless adenovirus backbone for generation of fusion gene recombinant adenovirus. These fusion gene recombinant viruses can be used as a virus-form to immunize patients directly or alternatively, to infected RCC cells or DC to generate kidney cancer vaccine for the direct immunization of patients. Alternatively, defined RCC cell lines can be stably transfected with pCEP4-GMCSF-G250 and used as RCC tumor vaccine. These various types of G250-GM-CSF vaccine formulations also can be used as an in-vitro immunostimulant for activation and propagation of G250 targeted CTL from PBMC or TIL cultures, which derived from patients with RCC then, re-infuses these CTL back to patients as an adoptive immunotherapy.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of inhibiting the proliferation or growth of a transformed renal cell that bears a G250 antigen, said method comprising:
   removing an immune cell from a mammalian host;
   activating the immune cell with a chimeric fusion protein comprising a human G250 kidney cancer-specific antigen attached to a human granulocyte macrophage colony stimulating factor (GM-CSF), wherein the human G250 antigen is encoded by the nucleotide sequence of SEQ ID NO:23 and the human GM-CSF is encoded by the nucleotide sequence of SEQ ID NO:24; and
   infusing the activated cell into an organism containing a transformed renal cell bearing a G250 antigen.

2. The method of claim 1, wherein the activating step comprises transfecting the immune cell with a nucleic acid encoding the chimeric fusion protein.

3. The method of claim 2, wherein the transfecting is by use of an agent that transfects a cell, wherein the agent is selected from the group consisting of a viral vector, a cationic lipid, a liposome, and a dendrimer.

4. The method of claim 1, wherein the immune cell is a dendritic cell, an antigen presenting cell, a B-cell, a T-cell, a monocyte, a peripheral blood lymphocyte, or a tumor infiltrating lymphocyte.

5. The method of claim 1, wherein the chimeric fusion protein comprises the amino acid sequence of SEQ ID NO:1.

6. The method of claim 1, wherein the activating step comprises contacting the immune cell with the chimeric fusion protein.

7. The method of claim 1, wherein the infusing step comprises infusing the activated cell into the mammalian host from which the immune cell was removed.

8. The method of claim 1, wherein after the activating step and prior to the infusing step, the method further comprises expanding the activated cell in culture.

9. The method of claim 1, wherein the mammalian host is a human.

10. A method of treating an individual having a renal cell cancer, said method comprising:
   (a) sensitizing antigen presenting cells in vitro with a sensitizing-effective amount of a chimeric fusion protein comprising a human G250 kidney cancer-specific antigen attached to a human granulocyte macrophage colony stimulating factor (GM-CSF), wherein the human G250 antigen is encoded by the nucleotide sequence of SEQ ID NO:23 and the human GM-C SF is encoded by the nucleotide sequence of SEQ ID NO:24; and
   (b) administering to an individual having the renal cell cancer or a metastasis thereof a therapeutically effective amount of the sensitized antigen presenting cells.

11. The method of claim 10, wherein the antigen presenting cells are autologous to the individual or are major histocompatibility complex (MHC)-matched allogenic dendritic cells.

12. The method of claim 10, wherein the sensitizing step comprises contacting the antigen presenting cells with the chimeric fusion protein.

13. The method of claim 10, wherein the sensitizing step comprises transfecting the antigen presenting cells with a nucleic acid encoding the chimeric fusion protein.

14. The method of claim 10, wherein the chimeric fusion protein comprises the amino acid sequence of SEQ ID NO:1.

15. The method of claim 10, wherein the antigen presenting cells are selected from the group consisting of dendritic cells, peripheral blood lymphocytes, monocytes, macrophages, fibroblasts, and tumor infiltrating lymphocytes.

16. The method of claim 10, wherein subsequent to the sensitizing step, the method further comprises expanding the sensitized antigen presenting cells in culture.

17. The method of claim 10, wherein the sensitized antigen presenting cells are administered systemically.

18. The method of claim 10, wherein the sensitized antigen presenting cells are administered intravenously.

* * * * *